US012654016B2

(12) United States Patent
Nanavati et al.

(10) Patent No.: US 12,654,016 B2
(45) Date of Patent: Jun. 16, 2026

(54) DEVICES AND METHODS FOR STIMULATING NEURAL TISSUE

(71) Applicant: Saluda Medical Pty Ltd, Macquarie Park (AU)

(72) Inventors: Zubin Nanavati, Macquarie Park (AU); Daniel John Parker, Macquarie Park (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 259 days.

(21) Appl. No.: 18/509,170

(22) Filed: Nov. 14, 2023

(65) Prior Publication Data

US 2024/0173550 A1 May 30, 2024

(30) Foreign Application Priority Data

Nov. 14, 2022 (AU) ................................. 2022903407

(51) Int. Cl.
*A61N 1/36* (2006.01)
*A61B 5/00* (2006.01)
(Continued)

(52) U.S. Cl.
CPC .......... *A61N 1/36157* (2013.01); *A61B 5/388* (2021.01); *A61B 5/4836* (2013.01);
(Continued)

(58) Field of Classification Search
CPC .. A61N 1/36157; A61N 1/08; A61N 1/36139; A61N 1/36175; A61B 5/388; A61B 5/4836; A61B 5/686
See application file for complete search history.

(56) References Cited

U.S. PATENT DOCUMENTS 6,381,496 B1 4/2002 Meadows et al.
6,473,653 B1 10/2002 Schallhorn et al.
(Continued)

FOREIGN PATENT DOCUMENTS

AU 2020100330 A4 9/2020
WO WO2001043818 A1 6/2001
(Continued)

OTHER PUBLICATIONS

U.S. Appl. No. 60/383,157, filed May 23, 2002, Ayal et al.
(Continued)

*Primary Examiner* — Eugene T Wu
(74) *Attorney, Agent, or Firm* — Barnes & Thornburg LLP

(57) ABSTRACT

In some implementations, the device may include a neural stimulation system having: an implantable closed-loop neural stimulation device for controllably delivering neural stimuli via one or more stimulus electrodes, the device having the one or more stimulus electrodes and a feedback controller configured to adjust a stimulus intensity parameter so as to maintain a measured neural response intensity at a target response intensity; and a processor configured to: estimate an out-of-compliance current limit for each of the one or more stimulus electrodes; estimate a closed-loop current requirement for the implantable closed-loop neural stimulation device; compare the out-of-compliance current limit for each of the one or more stimulus electrodes to the closed-loop current requirement; and take a mitigating action based on the comparison.

20 Claims, 13 Drawing Sheets

(51) Int. Cl.
　　*A61B 5/388*　　　(2021.01)
　　*A61N 1/08*　　　(2006.01)

(52) U.S. Cl.
　　CPC ........... *A61N 1/08* (2013.01); *A61N 1/36139*
　　　　(2013.01); *A61N 1/36175* (2013.01); *A61B*
　　　　　　　　　　　　　　　　*5/686* (2013.01)

(56)　　　　　References Cited

U.S. PATENT DOCUMENTS

| | | | |
|---|---|---|---|
| 6,909,917 | B2 | 6/2005 | Woods et al. |
| 7,216,000 | B2 | 5/2007 | Sieracki et al. |
| 7,616,999 | B2 | 11/2009 | Overstreet et al. |
| 7,801,615 | B2 | 9/2010 | Meadows et al. |
| 8,412,345 | B2 | 4/2013 | Moffitt |
| 8,447,408 | B2 | 5/2013 | North et al. |
| 8,447,413 | B2 | 5/2013 | Stone et al. |
| 8,755,898 | B2 | 6/2014 | Goddard et al. |
| 8,792,982 | B2 | 7/2014 | Miesel et al. |
| 8,812,124 | B2 | 8/2014 | Lee |
| 8,818,516 | B2 | 8/2014 | Bloemer |
| 8,843,209 | B2 | 9/2014 | Wacnik et al. |
| 8,909,350 | B2 | 12/2014 | Lee |
| 8,918,177 | B2 | 12/2014 | Gauthier |
| 9,014,820 | B2 | 4/2015 | Lee et al. |
| 9,044,610 | B2 | 6/2015 | Rosenberg et al. |
| 9,072,903 | B2 | 7/2015 | Kaula et al. |
| 9,079,018 | B2 | 7/2015 | Olsen |
| 9,174,048 | B2 | 11/2015 | Polefko et al. |
| 9,174,052 | B1 | 11/2015 | Nabutovsky et al. |
| 9,302,113 | B2 | 4/2016 | Ranu et al. |
| 9,358,390 | B2 | 6/2016 | Polefko et al. |
| 9,381,357 | B2 | 7/2016 | Min et al. |
| 9,737,719 | B2 | 8/2017 | Skelton et al. |
| 9,827,424 | B2 | 11/2017 | Kaula et al. |
| 9,907,957 | B2 | 3/2018 | Woods et al. |
| 9,950,164 | B2 | 4/2018 | Lipani |
| 9,950,171 | B2 | 4/2018 | Johanek et al. |
| 10,537,741 | B2 | 1/2020 | Bradley et al. |
| 10,668,276 | B2 | 6/2020 | Kaula et al. |
| 10,729,905 | B2 | 8/2020 | Annoni et al. |
| 10,843,001 | B2 | 11/2020 | Parker |
| 10,967,186 | B2 | 4/2021 | Kaula et al. |
| 11,090,493 | B2 | 8/2021 | Hou et al. |
| 11,173,308 | B2 | 11/2021 | Brill et al. |
| 11,173,312 | B2 | 11/2021 | Gryzwa et al. |
| 11,260,232 | B2 | 3/2022 | Kaula et al. |
| 11,298,550 | B2 | 4/2022 | Howard et al. |
| 11,395,625 | B2 | 7/2022 | Clark et al. |
| 11,433,238 | B2 | 9/2022 | Fisher et al. |
| 11,571,578 | B2 | 2/2023 | Acklin et al. |
| 11,596,796 | B2 | 3/2023 | Min et al. |
| 11,660,452 | B2 | 5/2023 | Kent et al. |
| 11,672,978 | B2 | 6/2023 | Su et al. |
| 11,712,564 | B2 | 8/2023 | Miocinovic et al. |
| 11,779,775 | B1 | 10/2023 | John et al. |
| 11,786,738 | B1 | 10/2023 | John et al. |
| 11,806,538 | B2 | 11/2023 | Kibler et al. |
| 11,839,766 | B2 | 12/2023 | Scheltienne et al. |
| 11,850,426 | B2 | 12/2023 | Moffitt et al. |
| 11,865,347 | B2 | 1/2024 | Lee et al. |
| 2007/0185409 | A1 | 8/2007 | Wu et al. |
| 2016/0367826 | A1 | 12/2016 | Kothandaraman et al. |
| 2017/0120056 | A1 | 5/2017 | Woods et al. |
| 2018/0104489 | A1 | 4/2018 | Hershey et al. |
| 2018/0104493 | A1 | 4/2018 | Doan et al. |
| 2020/0016408 | A1 | 1/2020 | Perryman et al. |
| 2020/0046980 | A1 | 2/2020 | Moffitt et al. |
| 2020/0147388 | A1 | 5/2020 | Huertas Fernandez et al. |
| 2020/0147390 | A1 | 5/2020 | Zhang et al. |
| 2020/0147391 | A1 | 5/2020 | Moffitt et al. |
| 2020/0147397 | A1 | 5/2020 | Huertas Fernandez et al. |
| 2021/0008371 | A1 | 1/2021 | Annecchino et al. |
| 2021/0265033 | A1 | 8/2021 | Skelton et al. |
| 2021/0299448 | A1 | 9/2021 | Doan et al. |
| 2021/0379383 | A1* | 12/2021 | Single .................. A61N 1/16 |
| 2022/0079501 | A1 | 3/2022 | Zottola et al. |
| 2022/0111213 | A1 | 4/2022 | Cassar et al. |
| 2022/0118260 | A1 | 4/2022 | Zhu et al. |
| 2022/0134118 | A1 | 5/2022 | Johnson |
| 2022/0143410 | A1 | 5/2022 | Kyani et al. |
| 2022/0218995 | A1 | 7/2022 | Block et al. |
| 2022/0226658 | A1 | 7/2022 | Zenisek et al. |
| 2022/0241582 | A1 | 8/2022 | Huertas Fernandez et al. |
| 2022/0257943 | A1 | 8/2022 | Su |
| 2022/0266033 | A1 | 8/2022 | Jackson et al. |
| 2022/0323758 | A1 | 10/2022 | Zhang et al. |
| 2022/0387803 | A1 | 12/2022 | Zenisek et al. |
| 2023/0173274 | A1 | 6/2023 | Lee |
| 2023/0181914 | A1 | 6/2023 | Zenisek |
| 2023/0201603 | A1 | 6/2023 | Zhang et al. |
| 2023/0241395 | A1 | 8/2023 | Zenisek et al. |
| 2023/0248974 | A1 | 8/2023 | Dawson |
| 2023/0277849 | A1 | 9/2023 | Moffitt et al. |
| 2023/0338737 | A1 | 10/2023 | Lee |
| 2023/0381521 | A1 | 11/2023 | Dinsmoor et al. |
| 2023/0397875 | A1 | 12/2023 | Min et al. |

FOREIGN PATENT DOCUMENTS

| | | |
|---|---|---|
| WO | WO2002009808 A1 | 2/2002 |
| WO | WO2003043690 A1 | 5/2003 |
| WO | WO2003099377 A1 | 12/2003 |
| WO | WO2004034879 A3 | 7/2004 |
| WO | WO2004041351 B1 | 7/2004 |
| WO | WO2005089646 A1 | 9/2005 |
| WO | WO2005105202 A1 | 11/2005 |
| WO | WO2006112852 A2 | 10/2006 |
| WO | WO2006119046 A1 | 11/2006 |
| WO | WO2007018793 A1 | 2/2007 |
| WO | WO2007064924 A1 | 6/2007 |
| WO | WO2008005153 A3 | 4/2008 |
| WO | WO2008052085 A1 | 5/2008 |
| WO | WO2009015005 A1 | 1/2009 |
| WO | WO2009048775 A1 | 4/2009 |
| WO | WO2010005779 A1 | 1/2010 |
| WO | WO2010005818 A1 | 1/2010 |
| WO | WO2010005827 A1 | 1/2010 |
| WO | WO2010006090 A1 | 1/2010 |
| WO | WO2010005809 A3 | 5/2010 |
| WO | WO2010005771 A9 | 7/2010 |
| WO | WO2010057046 A3 | 8/2010 |
| WO | WO2010088417 A1 | 8/2010 |
| WO | WO2010093720 A1 | 8/2010 |
| WO | WO2010062622 A3 | 9/2010 |
| WO | WO2010126538 A1 | 11/2010 |
| WO | WO2010126539 A1 | 11/2010 |
| WO | WO2010005832 A3 | 12/2010 |
| WO | WO2011005607 A1 | 1/2011 |
| WO | WO2011014570 A1 | 2/2011 |
| WO | WO2011019933 A1 | 2/2011 |
| WO | WO2011085206 A3 | 9/2011 |
| WO | WO2011137193 A1 | 11/2011 |
| WO | WO2011159527 A3 | 12/2011 |
| WO | WO2012036883 A1 | 3/2012 |
| WO | WO2012162349 A1 | 11/2012 |
| WO | WO2012166656 A3 | 4/2013 |
| WO | WO2013075019 A1 | 5/2013 |
| WO | WO2013090675 A1 | 6/2013 |
| WO | WO2014058650 A1 | 4/2014 |
| WO | WO2014150001 A1 | 9/2014 |
| WO | WO2014036079 A3 | 10/2014 |
| WO | WO2014159896 A1 | 10/2014 |
| WO | WO2014145222 A3 | 12/2014 |
| WO | WO2014197596 A1 | 12/2014 |
| WO | WO2014210373 A1 | 12/2014 |
| WO | WO2015013398 A1 | 1/2015 |
| WO | WO2015044945 A1 | 4/2015 |
| WO | WO2015179177 A1 | 11/2015 |
| WO | WO2016004230 A1 | 1/2016 |
| WO | WO2016048756 A1 | 3/2016 |
| WO | WO2016048951 A1 | 3/2016 |
| WO | WO2016048967 A1 | 3/2016 |
| WO | WO2016048974 A1 | 3/2016 |
| WO | WO2016048976 A1 | 3/2016 |

(56) References Cited

FOREIGN PATENT DOCUMENTS

| | | | |
|---|---|---|---|
| WO | WO2016048968 A3 | 5/2016 |
| WO | WO2016069157 A1 | 5/2016 |
| WO | WO2016130454 A1 | 8/2016 |
| WO | WO2016191807 A1 | 12/2016 |
| WO | WO2017003946 A1 | 1/2017 |
| WO | WO2017019191 A1 | 2/2017 |
| WO | WO2017035140 A1 | 3/2017 |
| WO | WO2017048963 A1 | 3/2017 |
| WO | WO2017053237 A1 | 3/2017 |
| WO | WO2017066187 A1 | 4/2017 |
| WO | WO2017117434 A1 | 7/2017 |
| WO | WO2017160442 A1 | 9/2017 |
| WO | WO2017218400 A1 | 12/2017 |
| WO | WO2018038794 A1 | 3/2018 |
| WO | WO2018053336 A1 | 3/2018 |
| WO | WO2018039296 A3 | 4/2018 |
| WO | WO2018067239 A1 | 4/2018 |
| WO | WO2018071865 A1 | 4/2018 |
| WO | WO2018080753 A1 | 5/2018 |
| WO | WO2018080887 A1 | 5/2018 |
| WO | WO2018097918 A1 | 5/2018 |
| WO | WO2018119220 A1 | 6/2018 |
| WO | WO2018132529 A1 | 7/2018 |
| WO | WO2018132535 A1 | 7/2018 |
| WO | WO2018140864 A1 | 8/2018 |
| WO | WO2018182881 A1 | 10/2018 |
| WO | WO2018208992 A1 | 11/2018 |
| WO | WO2019005266 A1 | 1/2019 |
| WO | WO2019010225 A1 | 1/2019 |
| WO | WO2019032987 A1 | 2/2019 |
| WO | WO2019036180 A1 | 2/2019 |
| WO | WO2019067059 A1 | 4/2019 |
| WO | WO2019070406 A1 | 4/2019 |
| WO | WO2019074949 A1 | 4/2019 |
| WO | WO2019094109 A1 | 5/2019 |
| WO | WO2019118247 A1 | 6/2019 |
| WO | WO2019118577 A1 | 6/2019 |
| WO | WO2019136072 A1 | 7/2019 |
| WO | WO2019199558 A1 | 10/2019 |
| WO | WO2019210202 A1 | 10/2019 |
| WO | WO2019226564 A1 | 11/2019 |
| WO | WO2019226568 A1 | 11/2019 |
| WO | WO2020010120 A1 | 1/2020 |
| WO | WO2020041323 A1 | 2/2020 |
| WO | WO2019055688 A3 | 4/2020 |
| WO | WO2020150647 A1 | 7/2020 |
| WO | WO2020162990 A2 | 8/2020 |
| WO | WO2020163037 A1 | 8/2020 |
| WO | WO2020163041 A1 | 8/2020 |
| WO | WO2020163043 A1 | 8/2020 |
| WO | WO2020163044 A1 | 8/2020 |
| WO | WO2020163045 A1 | 8/2020 |
| WO | WO2020180433 A1 | 9/2020 |
| WO | WO2020206152 A1 | 10/2020 |
| WO | WO2021021325 A1 | 2/2021 |
| WO | WO2021021326 A1 | 2/2021 |
| WO | WO2021021327 A1 | 2/2021 |
| WO | WO2021021662 A1 | 2/2021 |
| WO | WO2021030152 A1 | 2/2021 |
| WO | WO2021080727 A1 | 4/2021 |
| WO | WO2021080834 A1 | 4/2021 |
| WO | WO2021158445 A1 | 8/2021 |
| WO | WO2021162717 A1 | 8/2021 |
| WO | WO2021178105 A1 | 9/2021 |
| WO | WO2021211357 A1 | 10/2021 |
| WO | WO2021221895 A1 | 11/2021 |
| WO | WO2021252259 A1 | 12/2021 |
| WO | WO2021262762 A1 | 12/2021 |
| WO | WO2022066652 A1 | 3/2022 |
| WO | WO2022104387 A1 | 5/2022 |
| WO | WO2022174233 A1 | 8/2022 |
| WO | WO2022177747 A1 | 8/2022 |
| WO | WO2022182536 A1 | 9/2022 |
| WO | WO2022182656 A1 | 9/2022 |
| WO | WO2022182827 A1 | 9/2022 |
| WO | WO2022182860 A1 | 9/2022 |
| WO | WO2022183201 A1 | 9/2022 |
| WO | WO2022220956 A1 | 10/2022 |
| WO | WO2022232036 A1 | 11/2022 |
| WO | WO2022240579 A1 | 11/2022 |
| WO | WO2022240580 A1 | 11/2022 |
| WO | WO2022245970 A1 | 11/2022 |
| WO | WO2023039361 A1 | 3/2023 |
| WO | WO2023049660 A1 | 3/2023 |
| WO | WO2023064081 A1 | 4/2023 |
| WO | WO2023069848 A1 | 4/2023 |
| WO | WO2023102433 A1 | 6/2023 |
| WO | WO2023107444 A1 | 6/2023 |
| WO | WO2023115145 A1 | 6/2023 |
| WO | WO2023137009 A1 | 7/2023 |
| WO | WO2023137384 A1 | 7/2023 |
| WO | WO2023149987 A1 | 8/2023 |
| WO | WO2023164700 A1 | 8/2023 |
| WO | WO2023200583 A1 | 10/2023 |
| WO | WO2023250241 A1 | 12/2023 |

OTHER PUBLICATIONS

Alam et al., "Evaluation of optimal electrode configurations for epidural spinal cord stimulation in cervical spinal cord injured rats", Journal of Neuroscience Methods, Mar. 2015, 28 pgs.

Connolly et al., "Towards a platform for prototyping control systems for optimization of neuromodulation therapies", IEEE Biomedical Circuits and Systems Conference (BioCAS), 2015, pp. 1-4.

Kent, "Characterization of Evoked Potentials During Deep Brain Stimulation in the Thalamus", "2013, Dissertation, Duke University. Retrieved from https://hdl.handle.net/10161/8195. https://dukespace.lib.duke.edu/dspace/handle/10161/8195".

Oakley et al., "Transverse Tripolar Spinal Cord Stimulation: Results of an International Multicenter Study", Neuromodulation, vol. 9, No. 3, 2006, pp. 192-203.

Rijkhoff et al., "Acute Animal Studies on the Use of Anodal Block to Reduce Urethral Resistance in Sacral Root Stimulation", IEEE Transactions on Rehabilitation Engineering, 1994, vol. 2, No. 2, pp. 92-99.

Siegfried et al., "Bilateral Chronic Electrostimulation of Ventroposterolateral Pallidum: a New Therapeutic Approach for Alleviating all Parkinsonian Symptoms", Neurosurgery, 35, No. 6, Dec. 1994, pp. 1126-1130.

Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.

Yearwood, T. L. et al., "Pulse Width Programming in Spinal Cord Stimulation: a Clinical Study", Pain Physician. 2010. vol. 13, pp. 321-335.

* cited by examiner

700

710

720

Charger

Device

RC

750

CST

740

730

1400

DEVICES AND METHODS FOR STIMULATING NEURAL TISSUE

The present application claims priority from Australian Provisional Patent Application No 2022903407 filed on Nov. 14, 2022, the contents of which are incorporated herein by reference in their entirety.

TECHNICAL FIELD

The present invention relates to neuromodulation and in particular to methods for predicting and mitigating adverse events in a neural stimulation device.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation device applies an electrical pulse (stimulus) to neural tissue (fibres, or neurons) in order to generate a therapeutic effect. In general, the electrical stimulus generated by a neuromodulation device evokes a neural response known as an action potential in a neural fibre which then has either an inhibitory or excitatory effect. Inhibitory effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a device typically comprises an implanted electrical pulse generator, and a power source such as a battery that may be transcutaneously rechargeable by wireless means, such as inductive transfer. An electrode array is connected to the pulse generator, and is implanted adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates an action potential in the fibres. Action potentials propagate along the fibres in orthodromic (in afferent fibres this means towards the head, or rostral) and antidromic (in afferent fibres this means towards the cauda, or caudal) directions. Action potentials propagating along Aβ (A-beta) fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

For effective and comfortable neuromodulation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it is therefore desirable to apply stimuli with intensity below a discomfort threshold, above which uncomfortable or painful percepts arise due to over-recruitment of Aβ fibres. When recruitment is too large, Aβ fibres produce uncomfortable sensations. Stimulation at high intensity may even recruit Aδ (A-delta) fibres, which are sensory nerve fibres associated with acute pain, cold and heat sensation. It is therefore desirable to maintain stimulus intensity within a therapeutic range between the recruitment threshold and the discomfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Attempts have been made to address such problems by way of feedback or closed-loop control, such as using the methods set forth in International Patent Publication No. WO2012/155188 by the present applicant. Feedback control seeks to compensate for relative nerve/electrode movement by controlling the intensity of the delivered stimuli so as to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range.

It is therefore desirable to accurately measure the intensity and other characteristics of a neural response evoked by the stimulus. The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO2012/155183, the content of which is incorporated herein by reference.

Closed-loop neural stimulation therapy is governed by a number of parameters to which values must be assigned to implement the therapy. The effectiveness of the therapy depends in large measure on the suitability of the assigned parameter values to the patient undergoing the therapy. As patients vary significantly in their physiological characteristics, a "one-size-fits-all" approach to parameter value assignment is likely to result in ineffective therapy for a large proportion of patients. An important preliminary task, once a neuromodulation device has been implanted in a patient, is therefore to assign values to the therapy parameters that maximise the effectiveness of the therapy the device will deliver to that particular patient. This task is known as programming or fitting the device. Programming generally involves applying certain test stimuli via the device, recording responses, and based on the recorded responses, inferring or calculating the most effective parameter values for the patient. The resulting parameter values are then formed into a "program" that may be loaded to the device to govern subsequent therapy. Some of the recorded responses may be neural responses evoked by the test stimuli, which provide an objective source of information that may be analysed along with subjective responses elicited from the patient. In an effective programming system, the more responses that are analysed, the more effective the eventual assigned parameter values should be.

However, programming may be costly and time-consuming if unnecessarily prolonged. There is therefore an incentive to minimise the number of test stimuli to be applied and the amount of information to be recorded and analysed in order to produce the assigned values of the therapy parameters. In particular, the size of the therapy parameter search space is such that testing every possible combination of therapy parameters is impractical.

A neuromodulation device typically stimulates neural tissue by delivering pulses of constant current from a pulse generator via stimulus electrodes implanted adjacent to the neural tissue. A pulse generator may comprise one or more current sources and/or one or more current sinks configured to provide the constant current. The current sources and sinks draw power from a supply voltage rail. This arrangement means the pulse generator has an inherent upper limit on the current it can provide from a source or sink. A closed-loop controller of the kind described above will request the pulse generator to provide stimuli of varying current between pulses. If the requested stimulus current from a source or sink exceeds the upper limit, the current source or current sink will be unable to provide the requested current from the supply voltage rail. In such a situation, the current source or sink is said to go out of compliance. Out-of-compliance (OOC) events are undesirable during programming, because they limit the range of test stimuli that can be delivered to determine the most effective parameter values for the patient. Typically, if the device has an OOC event during programming, the programming will need to be re-started with a different stimulus electrode configuration. Out-of-compliance events during therapy are also undesirable because they indicate that the neuromodulation device is unable to deliver the required current for effective therapy.

Further complicating the situation, the OOC current limit for a source or sink within a pulse generator is not fixed, but depends on the value of the supply voltage rail (sometimes referred to herein as the compliance voltage) and the impedance of the load seen by the current source or sink, which largely consists of the tissue between the stimulus electrodes and the return electrodes. While the compliance voltage is known, the impedance of the load is highly variable between patients, between stimulus electrodes, and over time. It is therefore difficult to determine a single OOC current limit that is appropriate over all stimulus electrodes and all time for a given patient, let alone for all patients.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

Disclosed herein are methods of estimating the OOC current limit for a given stimulus electrode configuration using the stimulus parameter values and the measured electrode resistances, estimating a maximum stimulus current for effective neural stimulation therapy, and indicating if the latter exceeds the former. If it does, an OOC event is likely to occur during neural stimulation therapy with the current therapy parameters. Further disclosed are methods of pre-emptively mitigating such predicted OOC events by altering at least one stimulus parameter to either increase the OOC current limit or decrease the patient's maximum stimulus current so that the latter no longer exceeds the former.

Some implementations herein relate to a neural stimulation system. For example, a neural stimulation system may include an implantable device for controllably delivering neural stimuli, the device having: a plurality of electrodes including one or more stimulus electrodes and one or more measurement electrodes; a stimulus source configured to provide neural stimuli to be delivered via the one or more stimulus electrodes to a neural pathway of a patient in order to evoke neural responses from the neural pathway; measurement circuitry configured to capture signal windows from signals sensed on the neural pathway via the one or more measurement electrodes subsequent to respective neural stimuli; and a control unit configured to: control the stimulus source to provide a neural stimulus according to a stimulus intensity parameter; measure an intensity of an evoked neural response in a captured signal window subsequent to the neural stimulus; compute a feedback variable from the measured intensity of the evoked neural response; and adjust, using a feedback controller, the stimulus intensity parameter so as to maintain the feedback variable at a target response intensity. A neural stimulation system may also include a processor configured to: estimate an out-of-compliance current limit for each of the one or more stimulus electrodes; estimate a closed-loop current requirement for the implantable device; compare the out-of-compliance current limit for each of the one or more stimulus electrodes to the closed-loop current requirement; and take a mitigating action based on the comparison.

Some implementations herein relate to a method. For example, an automated method of controllably delivering neural stimuli to a neural pathway of a patient, may include delivering a neural stimulus to the neural pathway of the patient in order to evoke a neural response from the neural pathway, the neural stimulus being delivered according to a stimulus intensity parameter via one or more stimulus electrodes. The method may also include capturing a signal window from a signal sensed on the neural pathway subsequent to the delivered neural stimulus. The method may furthermore include measuring an intensity of a neural response evoked by the delivered neural stimulus in the captured signal window. The method may in addition include computing, from the measured intensity of the evoked neural response, a feedback variable. The method may moreover include adjusting the stimulus intensity parameter so as to maintain the feedback variable at a target response intensity. The method may also include estimating an out-of-compliance current limit for each of the one or more stimulus electrodes. The method may furthermore include estimating a closed-loop current requirement. The method may in addition include comparing the out-of-compliance current limit for each of the one or more stimulus electrodes to the closed-loop current requirement. The method may moreover include taking a mitigating action based on the comparison. Other embodiments of this aspect include corresponding computer systems, apparatus, and computer programs recorded on one or more computer storage devices, each configured to perform the actions of the methods.

Some implementations herein relate to a neural stimulation system. For example, a neural stimulation system may include an implantable closed-loop neural stimulation device for controllably delivering neural stimuli via one or more stimulus electrodes, the device having the one or more stimulus electrodes and a feedback controller configured to adjust a stimulus intensity parameter so as to maintain a measured neural response intensity at a target response intensity. The neural stimulation system may also include a processor configured to: estimate an out-of-compliance current limit for each of the one or more stimulus electrodes; estimate a closed-loop current requirement for the implantable closed-loop neural stimulation device; compare the out-of-compliance current limit for each of the one or more stimulus electrodes to the closed-loop current requirement; and take a mitigating action based on the comparison. Other embodiments of this aspect include corresponding computer systems, apparatus, and computer programs recorded on one or more computer storage devices, each configured to perform the actions of the methods.

Some implementations herein relate to a method. For example, a method of estimating a maximum stimulus current to be delivered to a patient by a neural stimulation device, may include estimating an evoked compound action potential (ECAP) threshold for the neural stimulation device based on neural stimuli delivered by the neural stimulation device, where the ECAP threshold is the intensity of the neural stimuli to be delivered above which neural recruitment occurs in a predetermined posture of the patient. The method may also include estimating the maximum stimulus current from the estimated ECAP threshold. Other embodiments of this aspect include corresponding computer systems, apparatus, and computer programs recorded on one or more computer storage devices, each configured to perform the actions of the methods.

Some implementations herein relate to a neural stimulation system. For example, a neural stimulation system may include an implantable device for controllably delivering neural stimuli, the device having: a plurality of electrodes including one or more stimulus electrodes; a stimulus source configured to provide neural stimuli to be delivered via the one or more stimulus electrodes to a neural pathway of a patient; and a control unit configured to: control the stimulus source to provide a neural stimulus according to a stimulus current and a further stimulus parameter. The neural stimulation system may also include a processor configured to: estimate an out-of-compliance current limit for each of the one or more stimulus electrodes; and choose a value for the further stimulus parameter such that the out-of-compliance current limit for each of the one or more stimulus electrodes exceeds a maximum value of the stimulus current.

Some implementations herein relate to a method. For example, an automated method of controllably delivering neural stimuli to a neural pathway of a patient, may include delivering a neural stimulus to the neural pathway of the patient in order to evoke a neural response from the neural pathway, the neural stimulus being delivered according to a stimulus current and a further stimulus parameter via one or more stimulus electrodes. The method may also include estimating an out-of-compliance current limit for each of the one or more stimulus electrodes. The method may furthermore include choosing a value for the further stimulus parameter such that the out-of-compliance current limit for each of the one or more stimulus electrodes is likely to exceed a maximum value of the stimulus current. Other embodiments of this aspect include corresponding computer systems, apparatus, and computer programs recorded on one or more computer storage devices, each configured to perform the actions of the methods.

References herein to estimation, determination, comparison and the like are to be understood as referring to an automated process carried out on data by a processor operating to execute a predefined procedure suitable to effect the described estimation, determination and/or comparison step(s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which.

DETAILED DESCRIPTION OF THE PRESENT TECHNOLOGY

Figure 1:
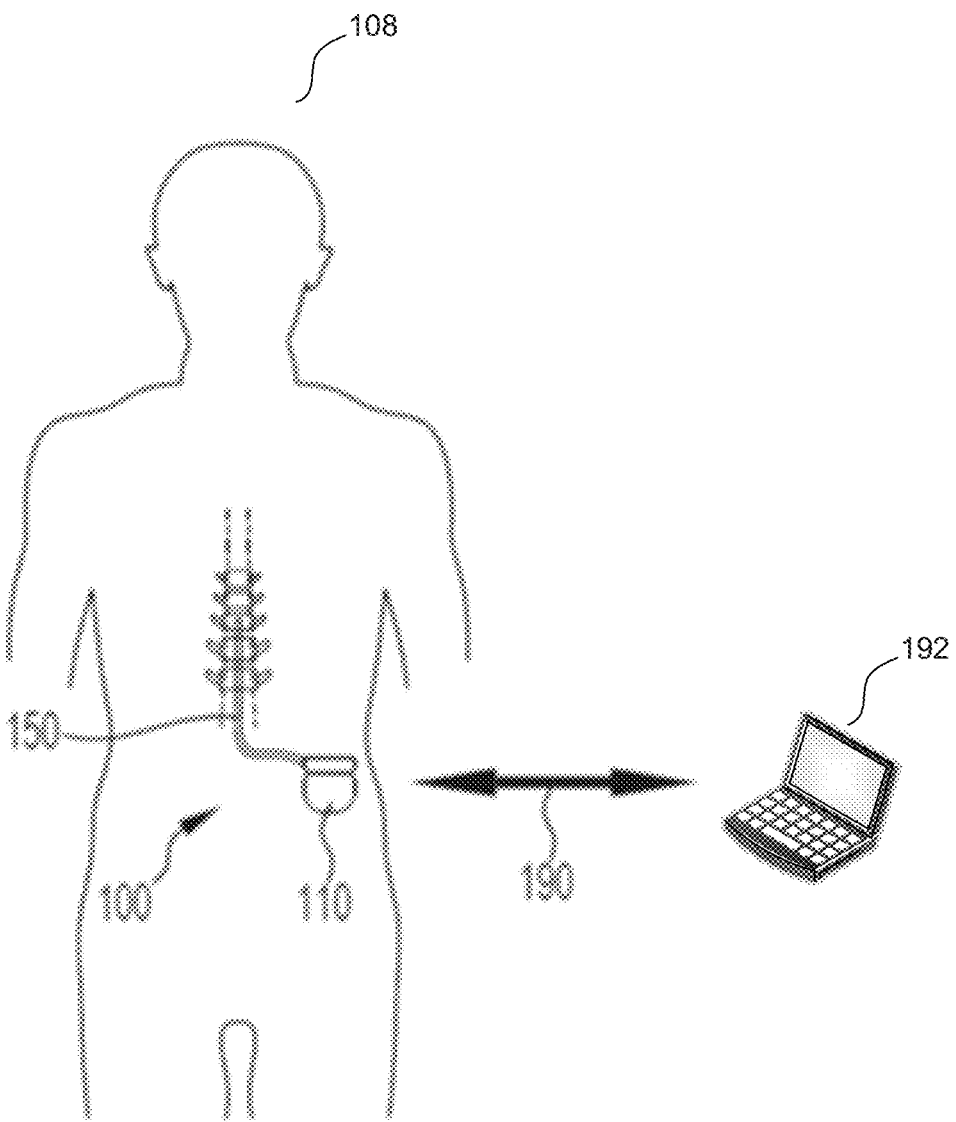
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as in a flank or sub-clavicularly. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. External device 192 may thus provide a clinical interface configured to program the implanted stimulator 100 and recover data stored on the implanted stimulator 100. This configuration is achieved by program instructions collectively referred to as the Clinical Programming Application (CPA) and stored in an instruction memory of the clinical interface.

Figure 2:
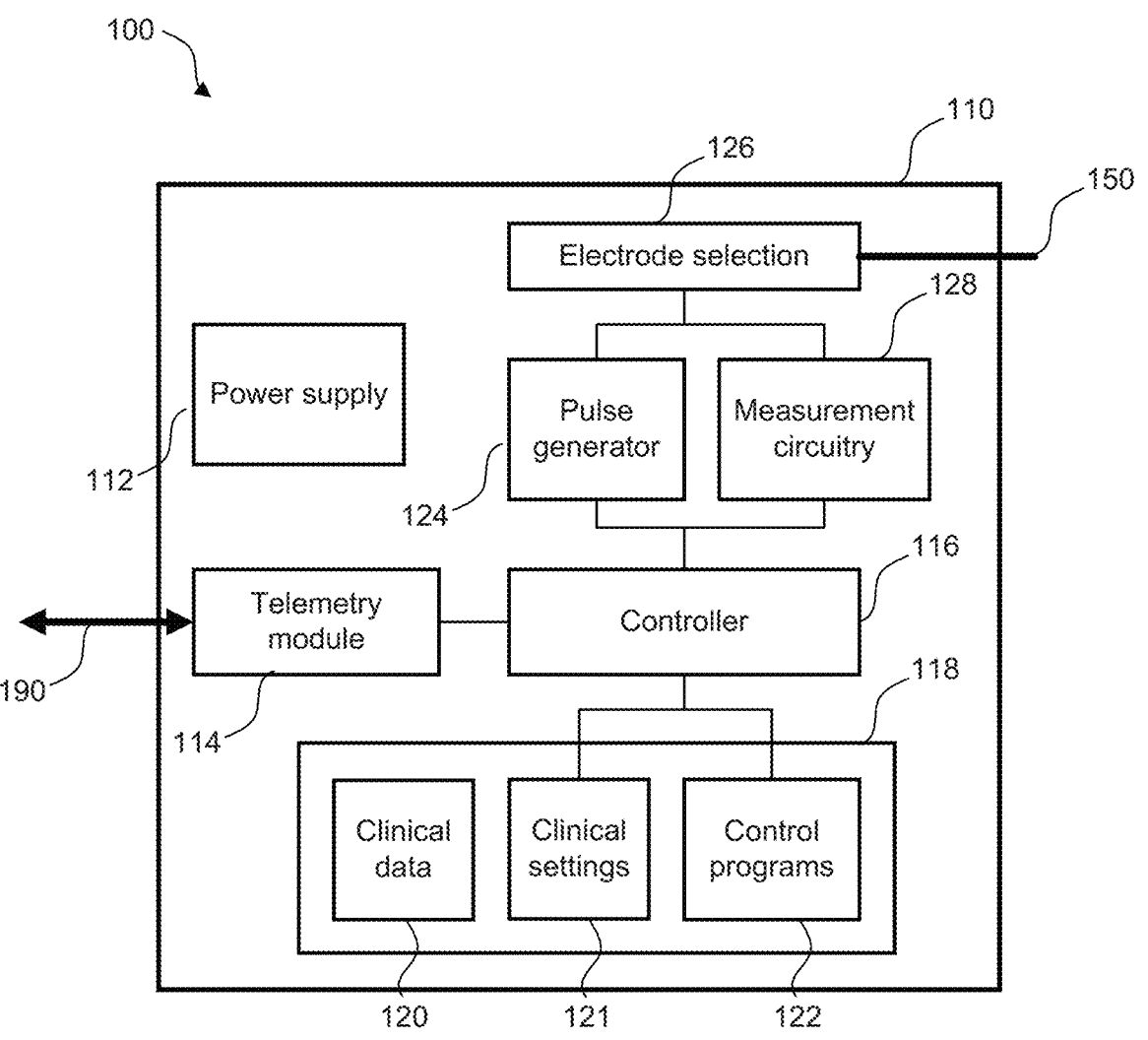
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communications channel 190, such as infrared (IR), radiofrequency (RF), capacitive and/or inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 is configured by control programs 122, sometimes referred to as firmware, to control a pulse generator 124 to generate stimuli, such as in the form of electrical pulses, in accordance with the clinical settings 121. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process signals comprising neural responses sensed at measurement electrode(s) of the electrode array 150 as selected by electrode selection module 126.

Figure 3:
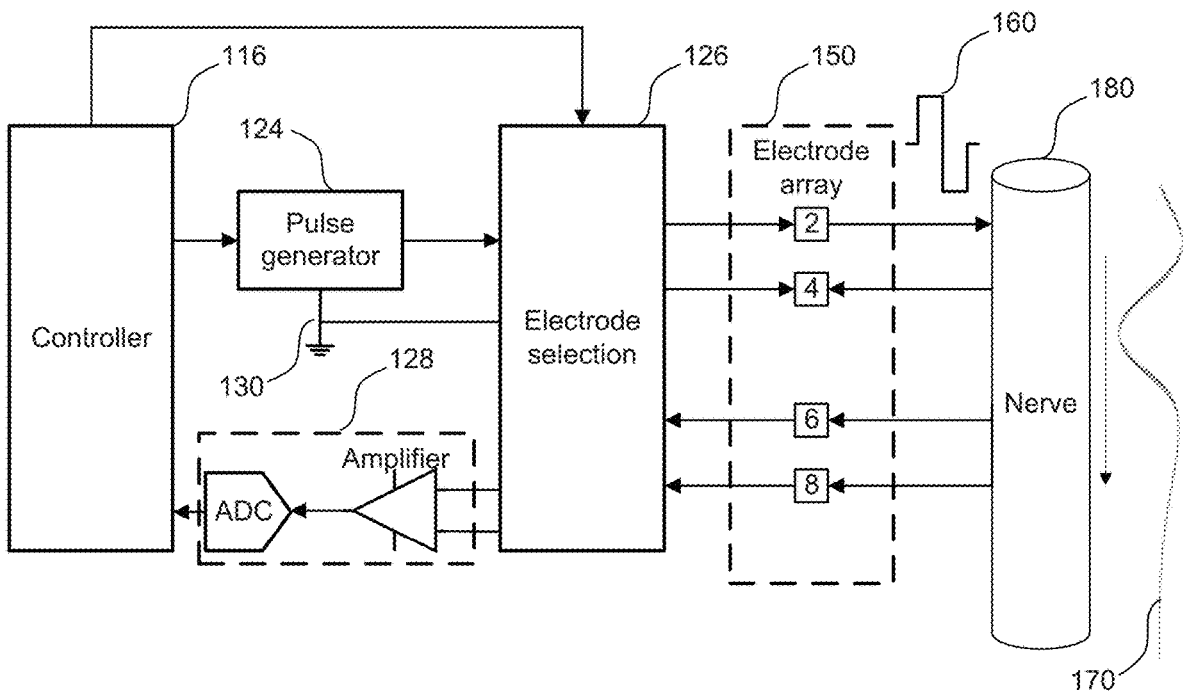
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g. a biphasic stimulus pulse 160 comprises two phases. Electrode selection module 126 also selects a return electrode 4 of the electrode array 150 for stimulus current return in each phase, to maintain a zero net charge transfer. The use of two electrodes in this manner for delivering and returning current in each stimulus phase is referred to as bipolar stimulation. Alternative embodiments may apply other forms of bipolar stimulation, or may use a greater number of stimulus and/or return electrodes. The set of stimulus electrodes and return electrodes is referred to as the stimulus electrode configuration. Electrode selection module 126 is illustrated as connecting to a ground 130 of the pulse generator 124 to enable stimulus current return via the return electrode 4. However, other connections for current return may be used in other implementations.

Delivery of an appropriate stimulus via electrodes 2 and 4 to the nerve 180 evokes a neural response 170 comprising an evoked compound action potential (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To program the stimulator 100 to the patient 108, a clinician may cause the stimulator 100 to deliver stimuli of various configurations which seek to produce a sensation that is experienced by the user as paraesthesia. When a stimulus electrode configuration is found which evokes paraesthesia in a location and of a size which is congruent with the area of the patient's body affected by pain and of a quality that is comfortable for the patient, the clinician or the patient nominates that configuration for ongoing use. The therapy parameters may be loaded into the memory 118 of the stimulator 100 as the clinical settings 121.

Figure 6:
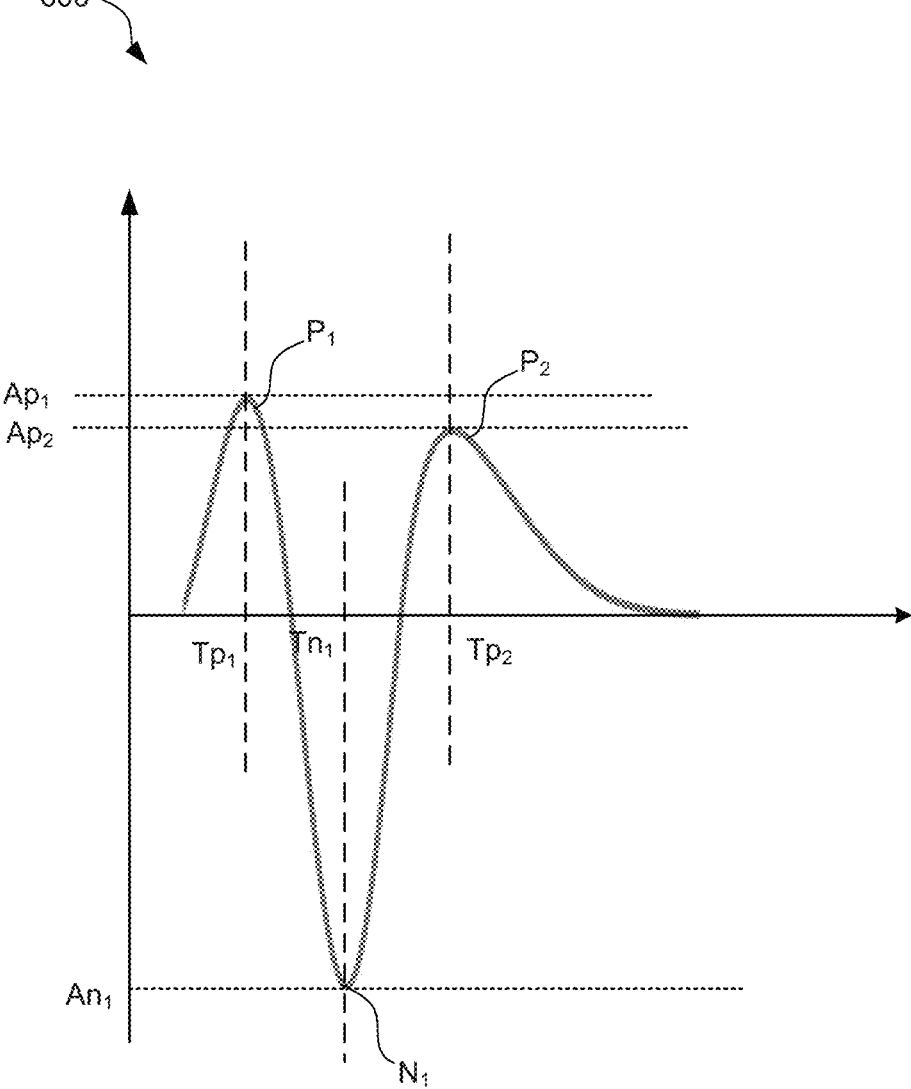
FIG. 6 illustrates the typical form of an electrically evoked compound action potential (ECAP) of a healthy subject.

FIG. 6 illustrates the typical form of an ECAP 600 of a healthy subject, as recorded at a single measurement electrode referenced to the system ground 130. The shape and duration of the single-ended ECAP 600 shown in FIG. 6 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Differential ECAP measurements are less subject to common-mode noise on the surrounding tissue than single-ended ECAP measurements. Depending on the polarity of recording, a differential ECAP may take an inverse form to that shown in FIG. 6, i.e. a form having two negative peaks N1 and N2, and one positive peak P1. Alternatively, depending on the distance between the two measurement electrodes, a differential ECAP may resemble the time derivative of the ECAP 600, or more generally the difference between the ECAP 600 and a time-delayed copy thereof.

The ECAP 600 may be characterised by any suitable characteristic(s) of which some are indicated in FIG. 6. The amplitude of the positive peak P1 is $Ap_1$ and occurs at time $Tp_1$. The amplitude of the positive peak P2 is $Ap_2$ and occurs at time $Tp_2$. The amplitude of the negative peak P1 is $An_1$ and occurs at time $Tn_1$. The peak-to-peak amplitude is $Ap_1+An_1$. A recorded ECAP will typically have a maximum peak-to-peak amplitude in the range of microvolts and a duration of 2 to 3 ms.

The stimulator 100 is further configured to measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and reference electrode 8, whereby the electrode selection module 126 selectively connects the chosen electrodes to the inputs of the measurement circuitry 128. Thus, signals sensed by the measurement electrodes 6 and 8 subsequent to the respective stimuli are passed to the measurement circuitry 128, which may comprise a differential amplifier and an analog-to-digital converter (ADC), as illustrated in FIG. 3. The recording electrode and the reference electrode are referred to as the measurement electrode configuration. The measurement circuitry 128 for example may operate in accordance with the teachings of the above-mentioned International Patent Publication No. WO2012/155183.

Signals sensed by the measurement electrodes 6, 8 and processed by measurement circuitry 128 are further processed by an ECAP detector implemented within controller 116, configured by control programs 122, to obtain information regarding the effect of the applied stimulus upon the nerve 180. In some implementations, the sensed signals are processed by the ECAP detector in a manner which measures and stores one or more characteristics from each evoked neural response or group of evoked neural responses contained in the sensed signal. In one such implementation, the characteristics comprise a peak-to-peak ECAP amplitude in microvolts ($\mu V$). For example, the sensed signals may be processed by the ECAP detector to determine the peak-to-peak ECAP amplitude in accordance with the teachings of International Patent Publication No. WO2015/074121, the contents of which are incorporated herein by reference. Alternative implementations of the ECAP detector may measure and store an alternative characteristic from the neural response, or may measure and store two or more characteristics from the neural response.

Stimulator 100 applies stimuli over a potentially long period such as days, weeks, or months and during this time may store characteristics of neural responses, clinical settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more characteristics such as a measure of the intensity of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

An activation plot, or growth curve, is an approximation to the relationship between stimulus intensity (e.g. an amplitude of the current pulse 160) and intensity of neural response 170 evoked by the stimulus (e.g. an ECAP amplitude). FIG. 4$a$ illustrates an idealised activation plot 402 for one posture of the patient 108. The activation plot 402 shows a linearly increasing ECAP amplitude for stimulus intensity values above a threshold 404 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 404 therefore reflects the field strength at which significant numbers of fibres begin to be recruited, and the increase in response intensity with stimulus intensity above the ECAP threshold reflects increasing numbers of fibres being recruited. Below the ECAP threshold 404, the ECAP amplitude may be taken to be zero. Above the ECAP threshold 404, the activation plot 402 has a positive, approximately constant slope indicating a linear relationship between stimulus intensity and the ECAP amplitude. Such a relationship may be modelled as:

$$y = \left\{ \begin{matrix} S(s-T), & s \geq T \\ 0, & s < T \end{matrix} \right\} \tag{1}$$

where s is the stimulus intensity, y is the ECAP amplitude, T is the ECAP threshold and S is the slope of the activation plot (referred to herein as the patient sensitivity). The slope S and the ECAP threshold T are the key parameters of the activation plot 402.

Figure 4A:
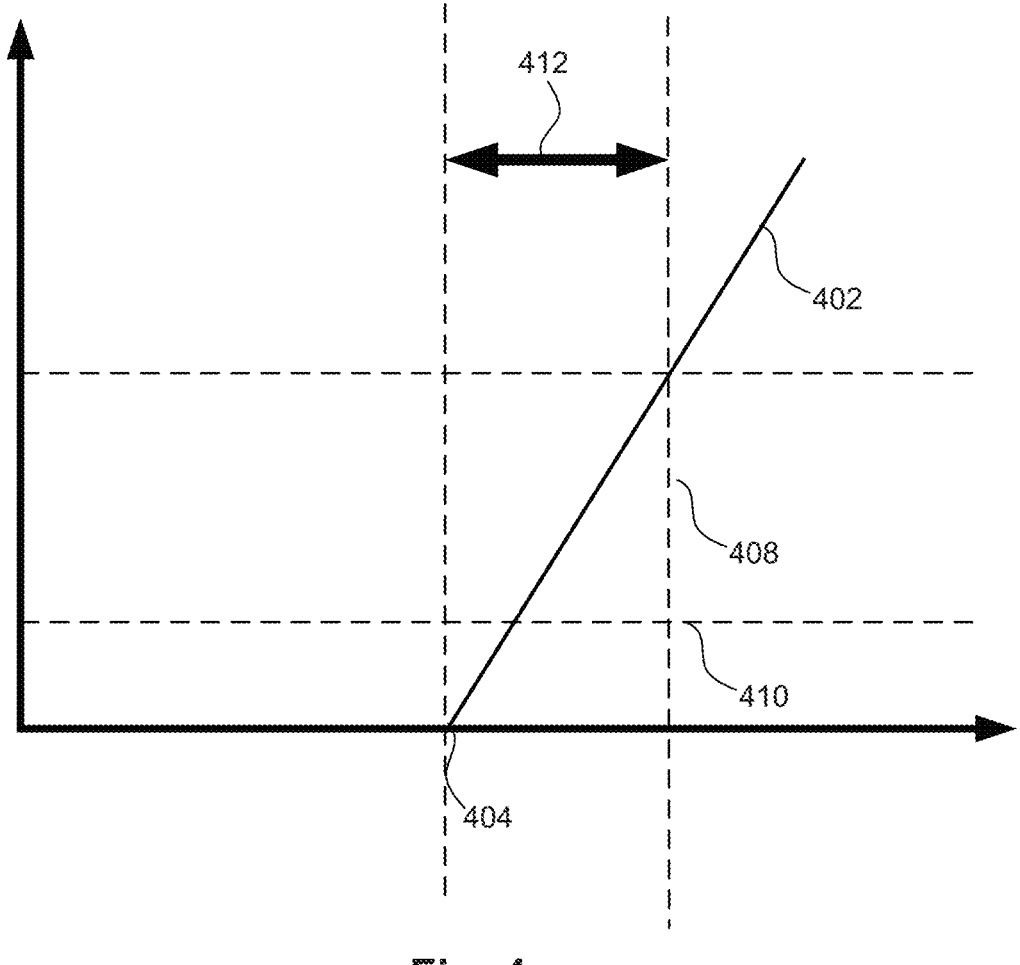
FIG. 4a illustrates an idealised activation plot for one posture of a patient undergoing neural stimulation.

FIG. 4a also illustrates a discomfort threshold 408, which is a stimulus intensity above which the patient 108 experiences uncomfortable or painful stimulation. FIG. 4a also illustrates a perception threshold 410. The perception threshold 410 corresponds to an ECAP amplitude that is barely perceptible by the patient. There are a number of factors which can influence the position of the perception threshold 410, including the posture of the patient. Perception threshold 410 may correspond to a stimulus intensity that is greater than the ECAP threshold 404, as illustrated in FIG. 4a, if patient 108 does not perceive low levels of neural activation. Conversely, the perception threshold 410 may correspond to a stimulus intensity that is less than the ECAP threshold 404, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it is desirable to maintain stimulus intensity within a therapeutic range. A stimulus intensity within a therapeutic range 412 is above the ECAP threshold 404 and below the discomfort threshold 408. In principle, it would be straightforward to measure these limits and ensure that stimulus intensity, which may be closely controlled, always falls within the therapeutic range 412. However, the activation plot, and therefore the therapeutic range 412, varies with the posture of the patient 108.

Figure 4B:
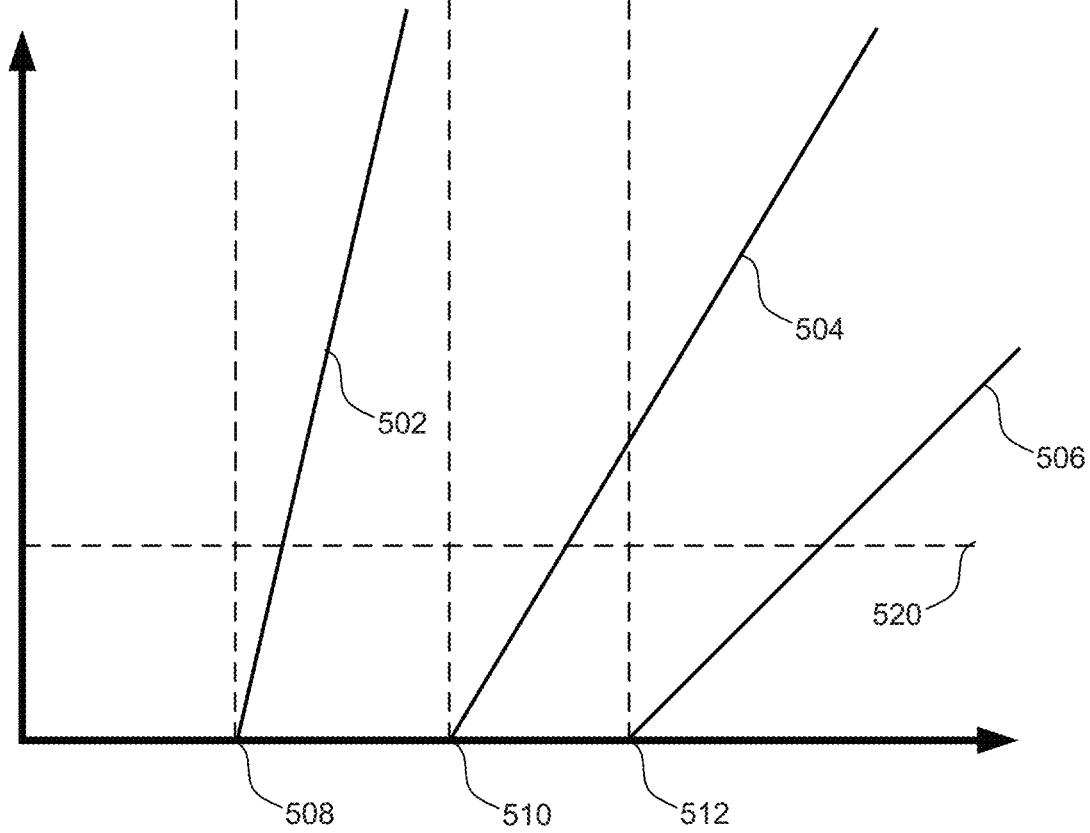
FIG. 4b illustrates the variation in the activation plots with changing posture of the patient.

FIG. 4b illustrates the variation in the activation plots with changing posture of the patient. A change in posture of the patient may cause a change in impedance of the electrode-tissue interface or a change in the distance between electrodes and the neurons. While the activation plots for only three postures, 502, 504 and 506, are shown in FIG. 4b, the activation plot for any given posture can lie between or outside the activation plots shown, on a continuously varying basis depending on posture. Consequently, as the patient's posture changes, the ECAP threshold changes, as indicated by the ECAP thresholds 508, 510, and 512 for the respective activation plots 502, 504, and 506. Additionally, as the patient's posture changes, the slope of the activation plot also changes, as indicated by the varying slopes of activation plots 502, 504, and 506. In general, as the distance between the stimulus electrodes and the spinal cord increases, the ECAP threshold increases and the slope of the activation plot decreases. The activation plots 502, 504, and 506 therefore correspond to increasing distance between stimulus electrodes and spinal cord, and decreasing patient sensitivity. The posture corresponding to the activation plot 502 may be said to be the most sensitive, while the posture corresponding to the activation plot 506 may be said to be the least sensitive.

To keep the applied stimulus intensity within the therapeutic range as patient posture varies, in some implementations an implantable neuromodulation device such as the stimulator 100 may adjust the applied stimulus intensity based on a feedback variable that is determined from one or more measured ECAP characteristics. In one implementation, the device may adjust the stimulus intensity to maintain the measured ECAP amplitude at a target response intensity. For example, the device may calculate an error between a target ECAP amplitude and a measured ECAP amplitude, and adjust the applied stimulus intensity to reduce the error as much as possible, such as by adding the scaled error to the current stimulus intensity. A neuromodulation device that operates by adjusting the applied stimulus intensity based on an measured ECAP characteristic is said to be operating in closed-loop mode and will also be referred to as a closed-loop neural stimulation (CLNS) device. By adjusting the applied stimulus intensity to maintain the measured ECAP amplitude at an appropriate target response intensity, such as a target ECAP amplitude 520 illustrated in FIG. 4b, a CLNS device will generally keep the stimulus intensity within therapeutic range as patient posture varies.

A CLNS device comprises a stimulator that takes a stimulus intensity value and converts it into a neural stimulus comprising a sequence of electrical pulses according to a predefined stimulation pattern. The stimulation pattern is parametrised by multiple stimulus parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The intensity of an evoked neural response (e.g. an ECAP) is measured by the CLNS device and compared to the target response intensity. The measured neural response intensity, and its deviation from the target response intensity, is used by the feedback loop to determine possible adjustments to the stimulus intensity parameter to maintain the neural response at the target intensity. If the target intensity is properly chosen, the patient receives consistently comfortable and therapeutic stimulation through posture changes and other perturbations to the stimulus/response behaviour.

Figure 5:
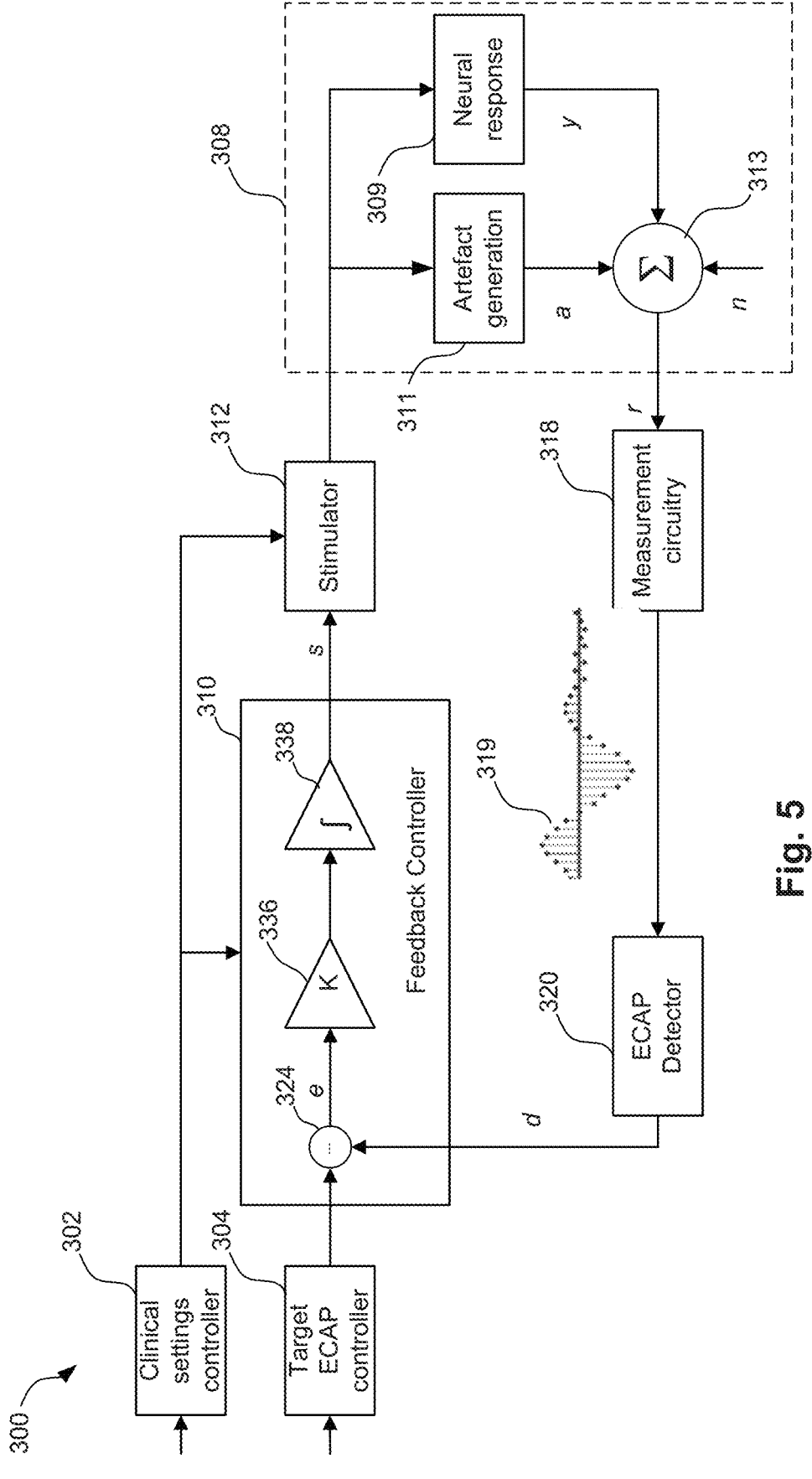
FIG. 5 is a schematic illustrating elements and inputs of a closed-loop neural stimulation (CLNS) system, according to one implementation of the present technology.

FIG. 5 is a schematic illustrating elements and inputs of a closed-loop neural stimulation (CLNS) system 300, according to one implementation of the present technology. The system 300 comprises a stimulator 312 which converts a stimulus intensity parameter (for example a stimulus current amplitude) s, in concert with a set of predefined stimulus parameters, to a neural stimulus comprising a sequence of electrical pulses on the stimulus electrodes (not shown in FIG. 5). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. Various sources of measurement noise n, as well as the artefact a, may add to the evoked response y at the summing element 313 to form the sensed signal r, including: electrical noise from external sources such as 50 Hz mains power; electrical disturbances produced by the body such as neural responses evoked not by the device but by other causes such as peripheral sensory input; EEG; EMG; and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

Measurement circuitry 318, which may be identified with measurement circuitry 128, amplifies the sensed signal r (including evoked neural response, artefact, and measurement noise), and samples the amplified sensed signal r to capture a "signal window" 319 comprising a predetermined number of samples of the amplified sensed signal r. The ECAP detector 320 processes the signal window 319 and outputs a measured neural response intensity d. In one implementation, the neural response intensity comprises a peak-to-peak ECAP amplitude. The measured response intensity d is input into the feedback controller 310. The feedback controller 310 comprises a comparator 324 that compares the measured response intensity d (an example of a feedback variable) to a target ECAP amplitude as set by the target ECAP controller 304 and provides an indication of the difference between the measured response intensity d and the target ECAP amplitude. This difference is the error value, e.

The feedback controller 310 calculates an adjusted stimulus intensity parameter, s, with the aim of maintaining a measured response intensity d equal to the target ECAP amplitude. Accordingly, the feedback controller 310 adjusts the stimulus intensity parameter s to minimise the error value, e. In one implementation, the controller 310 utilises a first order integrating function, using a gain element 336 and an integrator 338, in order to provide suitable adjustment to the stimulus intensity parameter s. According to such an implementation, the current stimulus intensity parameter s may be determined by the feedback controller 310 as $$s = \int Kedt \tag{2}$$

where K is the gain of the gain element 336 (the controller gain). This relation may also be represented as $$\delta s = Ke \tag{3}$$

where δs is an adjustment to the current stimulus intensity parameter s.

A target ECAP amplitude is input to the feedback controller 310 via the target ECAP controller 304. In one embodiment, the target ECAP controller 304 provides an indication of a specific target ECAP amplitude. In another embodiment, the target ECAP controller 304 provides an indication to increase or to decrease the present target ECAP amplitude. The target ECAP controller 304 may comprise an input into the CLNS system 300, via which the patient or clinician can input a target ECAP amplitude, or indication thereof. The target ECAP controller 304 may comprise memory in which the target ECAP amplitude is stored, and from which the target ECAP amplitude is provided to the feedback controller 310.

A clinical settings controller 302 provides clinical settings to the system 300, including the feedback controller 310 and the stimulus parameters for the stimulator 312 that are not under the control of the feedback controller 310. In one example, the clinical settings controller 302 may be configured to adjust the controller gain K of the feedback controller 310 to adapt the feedback loop to patient sensitivity. The clinical settings controller 302 may comprise an input into the CLNS system 300, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at a sampling frequency of 16 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus intensity is updated in light of the error value e.

Figure 7:
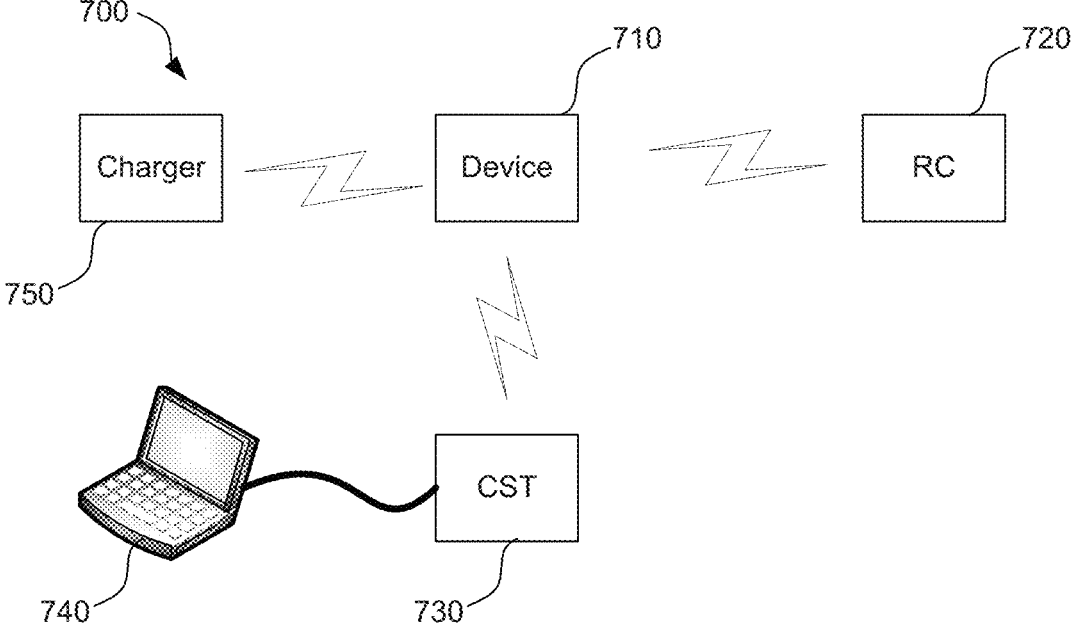
FIG. 7 is a block diagram of a neural stimulation therapy system including the implanted stimulator of FIG. 1 according to one implementation of the present technology.

FIG. 7 is a block diagram of a neural stimulation system 700. The neural stimulation system 700 is centred on a neuromodulation device 710. In one example, the neuromodulation device 710 may be implemented as the stimulator 100 of FIG. 1, implanted within a patient (not shown). The neuromodulation device 710 is connected wirelessly to a remote controller (RC) 720. The remote controller 720 is a portable computing device that provides the patient with control of their stimulation in the home environment by allowing control of the functionality of the neuromodulation device 710, including one or more of the following functions; enabling or disabling stimulation; adjustment of stimulus intensity or target response intensity; and selection of a stimulation control program from the control programs stored on the neuromodulation device 710.

The charger 750 is configured to recharge a rechargeable power source of the neuromodulation device 710. The recharging is illustrated as wireless in FIG. 7 but may be wired in alternative implementations.

The neuromodulation device 710 is wirelessly connected to a Clinical System Transceiver (CST) 730. The wireless connection may be implemented as the transcutaneous communications channel 190 of FIG. 1. The CST 730 acts as an intermediary between the neuromodulation device 710 and the Clinical Interface (CI) 740, to which the CST 730 is connected. A wired connection is shown in FIG. 7, but in other implementations, the connection between the CST 730 and the CI 740 is wireless.

The CI 740 may be implemented as the external computing device 192 of FIG. 1. The CI 740 is configured to program the neuromodulation device 710 and recover data stored on the neuromodulation device 710. This configuration is achieved by program instructions collectively referred to as the Clinical Programming Application (CPA) and stored in an instruction memory of the CI 740.

Assisted Programming System

As mentioned above, obtaining patient feedback about their sensations is important during programming of closed-loop neural stimulation therapy, but mediation by trained clinical engineers is expensive and time-consuming. It would therefore be advantageous if patients could program their own implantable device themselves, or with some assistance from a clinician. However, interfaces for current programming systems are non-intuitive and generally unsuitable for direct use by patients because of their technical nature. There is therefore a need for a CPA to be as intuitive for non-technical users as possible while avoiding discomfort to the patient. Implementations of an Assisted Programming System (APS) according to the present technology are generally configured to meet this need.

In some implementations, the APS comprises two elements: the Assisted Programming Module (APM), which forms part of the CPA, and the Assisted Programming Firmware (APF), which forms part of the control programs 122 executed by the controller 116 of the electronics module 110. The data obtained from the patient is analysed by the APM to determine the clinical settings for the neural stimulation therapy to be delivered by the stimulator 100. The APF is configured to complement the operation of the APM by responding to commands issued by the APM via the CST 730 to the stimulator 100 to deliver specified stimuli to the patient, and by returning, via the CST 730, measurements of neural responses to the delivered stimuli.

In other implementations, all the processing of the APS according to the present technology is done by the APF. In other words, the data obtained from the patient is not passed to the APM, but is analysed by the controller 116 of the device 710, configured by the APF, to determine the clinical settings for the neural stimulation therapy to be delivered by the stimulator 100.

In implementations of the APS in which the APM analyses the data from the patient, the APS instructs the device 710 to capture and return signal windows to the CI 740 via the CST 730. In such implementations, the device 710 captures the signal windows using the measurement circuitry 128 and bypasses the ECAP detector 320, storing the data representing the raw signal windows temporarily in memory 118 before transmitting the data representing the captured signal windows to the APS for analysis.

Following the programming, the APS may load the determined program onto the device 710 to govern subsequent neural stimulation therapy. In one implementation, the program comprises clinical settings 121, also referred to as therapy parameters, that are input to the neuromodulation device 710 by, or stored in, the clinical settings controller 302. The patient may subsequently control the device 710 to deliver the therapy according to the determined program using the remote controller 720 as described above. The determined program may also, or alternatively, be loaded into the CPA for validation and modification.

Estimating the Out-of-Compliance Current Limit

Figure 8:
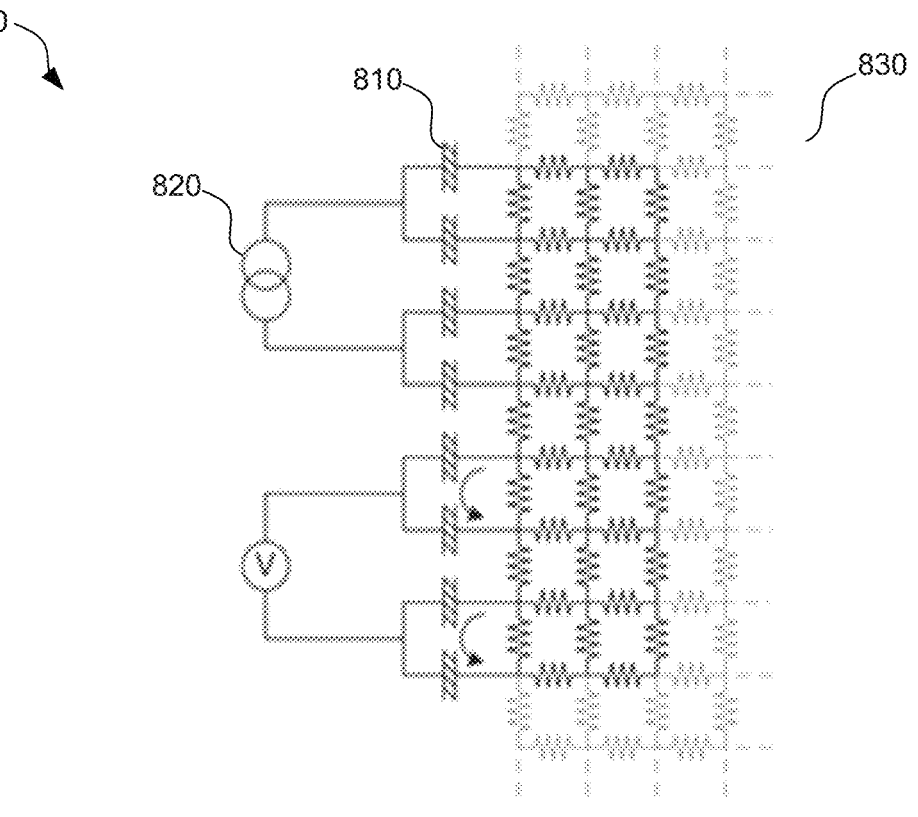
FIG. 8 contains a model of the Electrode-Tissue-Electrode interface of an implanted neuromodulation device.
Figure 9:
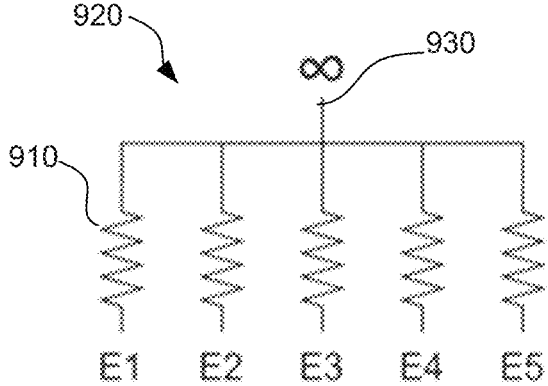
FIG. 9 illustrates a star network approximation to the resistor mesh in the model of FIG. 8.

FIG. 8 contains a model 800 of the Electrode-Tissue-Electrode Interface of an implanted neuromodulation device. The model 800 represents the load impedance Z seen by a current source 820 forming part of the pulse generator of a stimulator. The load impedance Z is dominated by the resistance of the tissue (modelled by the resistor mesh 830). The polarisation that occurs at the electrode-tissue interface is represented by the constant phase elements (CPEs) joining the mesh to the current source 820, e.g. the CPE 810. To simplify this analysis, the impedance of the CPEs has been excluded. The resistor mesh 830 in the model 800 may be approximated as a star network, as illustrated in FIG. 9. Each load resistance, e.g. the load resistance 910, in the star network 920 is the resistance to the "star point" 930 from the corresponding electrode, e.g. the electrode E1. The star point 930 represents a point in the tissue far distant from the electrode, so the resistance to the star point may be referred to as the "resistance to infinity" of the electrode. The star network model 920 of FIG. 9 loses accuracy as a model of the mesh 830 when the electrodes are physically close to one another due to field overlap.

To estimate the resistance to infinity of an electrode under test, a predetermined current may be sourced from the electrode under test and returned to ground on all other electrodes, which have first been connected together. When the current is flowing, the voltage difference between the electrode under test and the other electrodes may be measured. The measured impedance, computed as the ratio of the voltage difference and the predetermined current, is an acceptable estimate of the resistance to infinity (electrode resistance) from the electrode under test provided the number of other electrodes is large enough that the measured impedance is dominated by the resistance to infinity of the electrode under test. This condition is satisfied for an electrode array with sixteen electrodes, as is commonly used in a neuromodulation device.

Figures 10, 11:
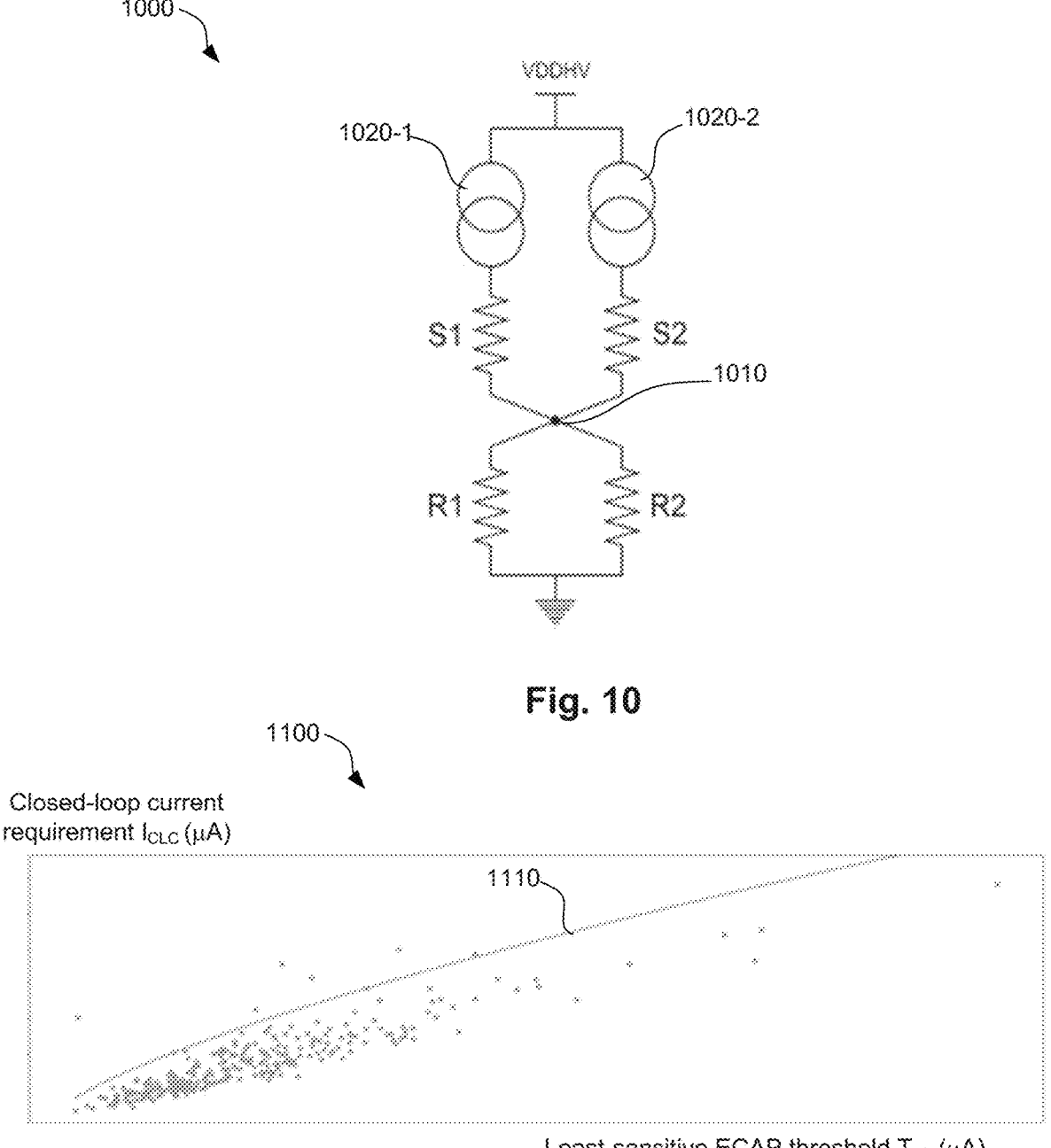
FIG. 10 is a simplified circuit representation of a neuromodulation device configured to source a current from a supply voltage rail to tissue via current sources and a pair of stimulus electrodes, and return the current from the tissue via a pair of return electrodes connected to ground.
FIG. 11 is a graph showing (as points) the maximum stimulus current produced by the stimulator of a closed-loop neural stimulation device over all postures for a number of patients.

FIG. 10 is a simplified circuit representation 1000 of a neuromodulation device configured to source a current from the supply voltage rail $V_{DDHV}$ to tissue via current sources 1020-1 and 1020-2 and a pair of stimulus electrodes, and return the current from the tissue via a pair of return electrodes connected to ground (a sourcing configuration). The point 1010 is the star point of the star network model 920 of tissue illustrated in FIG. 9. The stimulus electrodes have respective electrode resistances of $S_1$ and $S_2$, while the return electrodes have respective electrode resistances of $R_1$ and $R_2$. The return electrode resistances $R_1$ and $R_2$, being in parallel, can be combined into to a single equivalent return electrode resistance $R_T$:

$$R_T = \frac{1}{\frac{1}{R_1} + \frac{1}{R_2}} \tag{4}$$

The device has a total stimulus current output that is divided across all the stimulus electrodes according to some predetermined ratio. In FIG. 10, the stimulus current through the tissue is divided between the two current sources 1020-1 and 1020-2 according to respective fractions $\alpha_1$ and $\alpha_2$ whose sum is unity. The fractions $\alpha_1$ and $\alpha_2$ are stimulus parameters.

The current source 1020-x (where x is 1 or 2) goes out of compliance when the voltage across it falls to zero. This occurs at an out-of-compliance current limit $I_{OOC}$, which satisfies the equation $$V_{DDHV} = \alpha_x I_{OOC} S_x + I_{OOC} R_T \tag{5}$$

From Equation (5), the out-of-compliance current limit $I_{OOC}$ for the stimulus electrode x may be computed as $$I_{OOC} = \frac{V_{DDHV}}{\alpha_x S_x + R_T} \tag{6}$$

The APM or the APF, or some combination thereof, may estimate the electrode resistances of the respective electrodes of a given stimulus electrode configuration (SEC) in the manner described above. The APM or the APF, or some combination thereof, may then substitute the estimated electrode resistances, along with values for $V_{DDHV}$ and the stimulus parameter ax, into equations (4) and (6) to estimate the out-of-compliance current limit $I_{OOC}$ for each stimulus electrode x of the given SEC. This model works best when there is a large separation between the stimulus electrode(s) and the return electrode(s), but tests carried out using a saline bath to model the tissue have shown that the limit obtained by using the estimated electrode impedances and equation (6) is sufficiently accurate in most circumstances.

An equivalent simplified circuit representation to the circuit representation 1000 may be constructed for a neuromodulation device configured to sink a current from tissue to ground via two current sinks and a pair of stimulus electrodes, and return the current to the tissue via a pair of return electrodes connected to the supply voltage rail $V_{DDHV}$ (a sinking configuration). Because of the equivalence of this representation of the sinking configuration to the representation 1000 of a sourcing configuration, the same equations (4) and (6) may be used to estimate the out-of-compliance current limit $I_{OOC}$ for the sinking configuration for each stimulus electrode x of the given SEC. Therefore, if the neuromodulation device is configured to toggle between the sourcing and sinking configurations over the phases of a multi-phasic stimulus pulse, the out-of-compliance current limit $I_{OOC}$ is the same for each phase and therefore need only be estimated once for each stimulus electrode x of the given SEC.

Estimating the Closed-Loop Current Requirement

In a CLNS system, the stimulus current varies in order to maintain the measured neural response intensity at the target ECAP amplitude. The stimulus current required to maintain the measured neural response intensity at the target ECAP amplitude varies with posture, becoming generally greater as the posture becomes less sensitive. The maximum stimulus current required to maintain the measured neural response intensity at a comfortable target ECAP amplitude in the least sensitive posture is referred to herein as the closed-loop current requirement $(I_{CLC})$. In order for the patient to receive the full benefit of the CLNS therapy, the closed-loop current requirement $(I_{CLC})$ at a comfortable target ECAP amplitude should be less than the out-of-compliance current limit $I_{OOC}$.

FIG. 11 is a graph 1100 showing (as points) the maximum stimulus current produced by the stimulator of a CLNS device at a comfortable target ECAP amplitude over all postures for a number of patients, i.e. the closed-loop current requirement $(I_{CLC})$. Each value of the closed-loop current requirement $I_{CLC}$ is plotted against the ECAP threshold $T_{LS}$ in the least sensitive posture for that patient. The curve 1110 represents a power law function $y=Cx^{\alpha}$ fit to the $(T_{LS}, I_{CLC})$ value pairs such that 98% of the $I_{CLC}$ values fall below the curve 1110. Hence the equation $$I_{CLC} = CT_{LS}^{\alpha} \qquad (7)$$

where $\alpha$ is a power law parameter with a value in the range 0.0 to 1.0, in the range 0.2 to 0.9, in the range 0.3 to 0.8, or in the range 0.5 to 0.7, and C is a constant in the range 5 to 50, or in the range 10 to 40, or in the range 15 to 35, represents a conservative (high-sided) estimate of the closed-loop current requirement $I_{CLC}$ as a function of the least-sensitive-posture ECAP threshold $T_{LS}$. A similar model, with different parameter values, may be fit to values of the closed-loop current requirement $I_{CLC}$ as a function of the ECAP threshold $T_{LS}$ in other predetermined postures for that patient.

Figure 12:
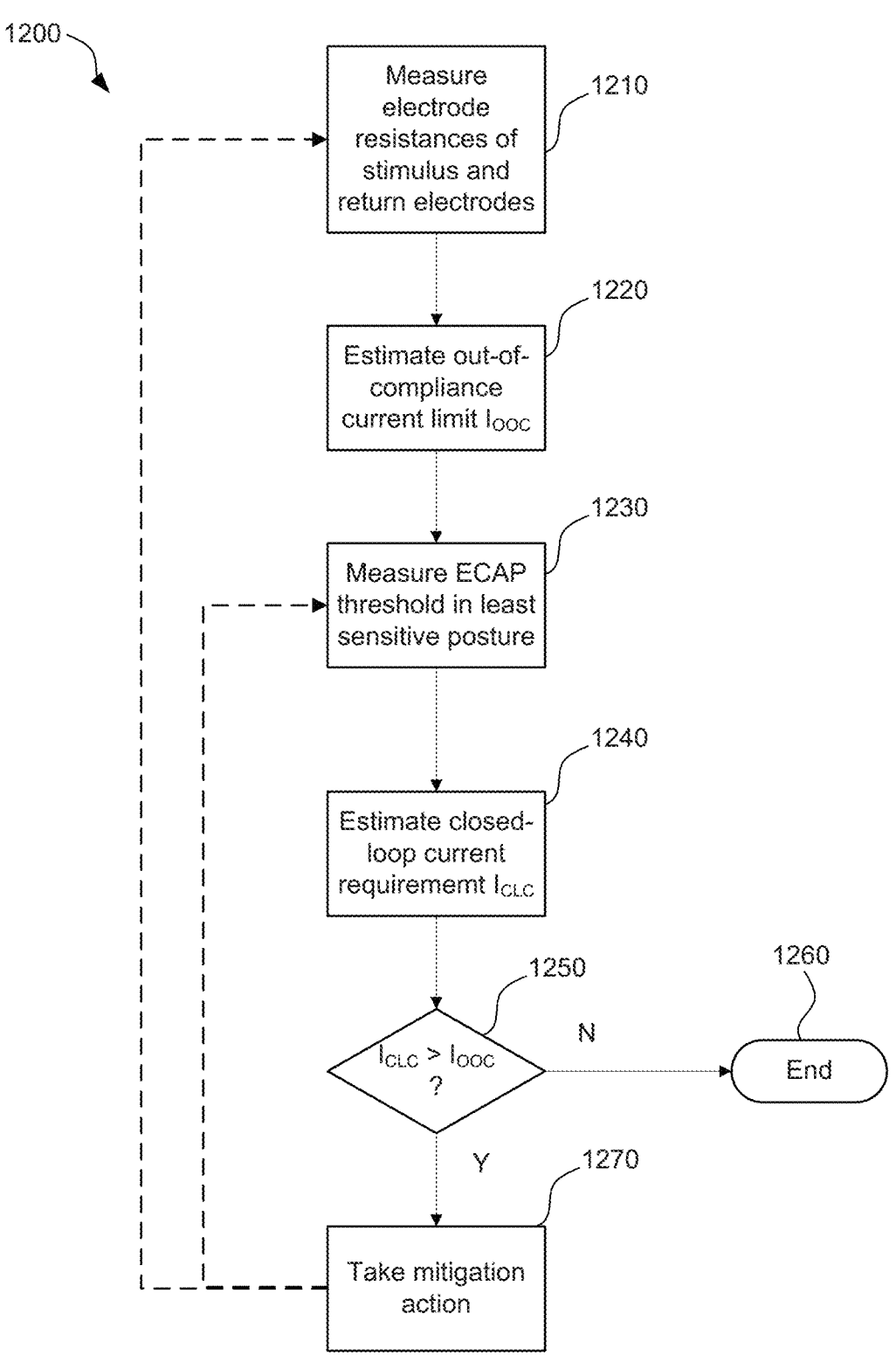
FIG. 12 is a flow chart illustrating a method of preemptively mitigating the risk of out-of-compliance events for the current therapy parameters of a closed-loop neural stimulation device according to one implementation of the present technology.

FIG. 12 is a flow chart illustrating a method 1200 of pre-emptively mitigating the risk of out-of-compliance events according to one aspect of the present technology. The method 1200 may be carried out during programming of a neuromodulation device 710 for CLNS therapy by the APM, the APF, or a combination of both as described above.

The method 1200 starts at step 1210, which measures the electrode resistances of the stimulus electrode(s) and return electrode(s) of the current SEC specified by the current therapy parameters. Step 1220 then applies equation (6), and possibly equation (4) if there is more than one return electrode in the SEC, to estimate the out-of-compliance current limit $I_{OOC}$ or for each stimulus electrode in the SEC.

The method 1200 then proceeds to step 1230, which measures the ECAP threshold $T_{LS}$ of the patient in the least sensitive posture. Methods of measuring the ECAP threshold are disclosed in, for example, the above-mentioned International Patent Publication No. WO2012/155188, the contents of which are herein incorporated by reference. Step 1240) then estimates the closed-loop current requirement $I_{CLC}$ of the patient from the least-sensitive-posture ECAP threshold $T_{LS}$ and Equation (7). Step 1250 then checks whether the closed-loop current requirement $I_{CLC}$ of the patient exceeds the out-of-compliance current limit $I_{OOC}$ for any stimulus electrode in the current SEC according to the current therapy parameters. If not ("N"), the risk of an out-of-compliance event is low, and the method 1200 ends (step 1260). If so ("Y"), there is a significant risk of an out-of-compliance event during CLNS therapy using the current therapy parameters. Step 1270 therefore takes an action to pre-emptively mitigate the risk. If step 1270 adjusts the therapy parameters, the method 1200 may then return to step 1210 to predict and possibly further mitigate any residual risk of out-of-compliance events with the new therapy parameters.

In some implementations, the mitigation action of step 1270 is simply to raise an indication to a user of the CPA that there is a risk of an out-of-compliance event. The user may then take whatever steps they deem suitable to mitigate that risk.

In some implementations of step 1270, the risk of out-of-compliance events is mitigated by increasing the out-of-compliance current limit $I_{OOC}$. In one such implementation, an alternative stimulus electrode configuration may be selected. In one example, more return electrodes are added to the SEC, and/or alternative return electrodes with lower electrode resistances are selected, to reduce the equivalent return electrode resistance $R_T$ and thereby increase $I_{OOC}$. Alternatively or additionally, an alternative stimulus electrode with a lower electrode resistance may be selected to replace the stimulus electrode whose electrode resistance is causing its out-of-compliance current limit $I_{OOC}$ to exceed the closed-loop current requirement $I_{CLC}$ of the patient in the current SEC.

In other implementations of step 1270, the risk of out-of-compliance events is mitigated by decreasing the patient's closed-loop current requirement $I_{CLC}$. Such implementations may be combined with, or employed as an alternative to, implementations which increase the out-of-compliance current limit $I_{OOC}$ as described above. In one such implementation, the stimulus pulse width may be increased to decrease the patient's closed-loop current requirement $I_{CLC}$. There is a relationship between the pulse width and the ECAP threshold T in a given posture such that increasing the stimulus pulse width generally decreases the ECAP threshold T. Therefore, in such an implementation, step 1270) may increase the stimulus pulse width by a small amount, say 80 μs, and the method 1200 may return to step 1230 to re-measure the ECAP threshold Tus in the least sensitive posture, and continue with steps 1240 to 1270.

Alternatively, to avoid having to re-measure the ECAP threshold, population statistics may be used to select an appropriate pulse width to mitigate the risk of OOC events during CLNS therapy.

Figure 13:
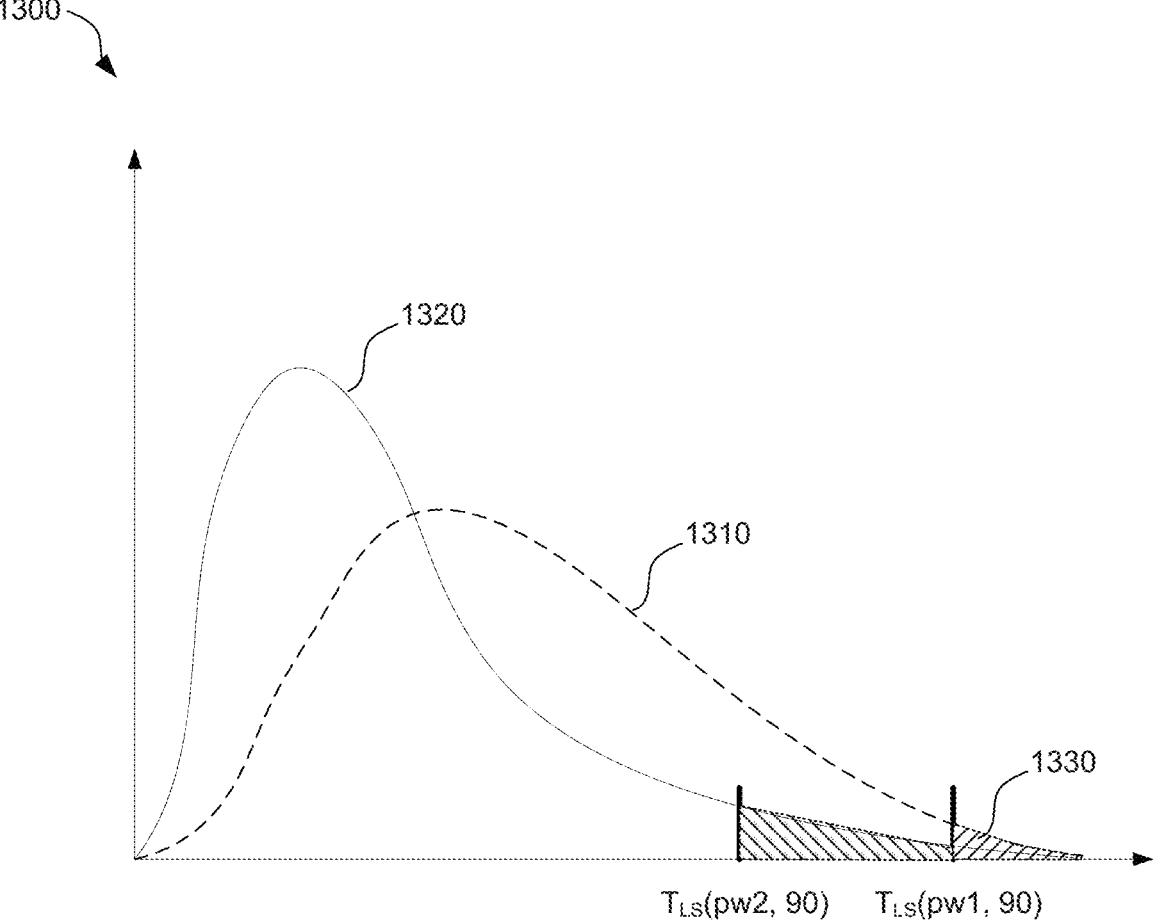
FIG. 13 is a graph containing two distributions of measured ECAP thresholds at two different pulse widths.

FIG. 13 is a graph 1300 containing two distributions 1310, 1320 of measured least-sensitive-posture ECAP thresholds $T_{LS}$ at two different pulse widths pw1 and pw2, where pw1<pw2. Also shown on each distribution is the 90th-percentile value of $T_{LS}$, written as $T_{LS}(pw1, 90)$ and $T_{LS}(pw2, 90)$. $T_{LS}(pw1, 90)$ is the value below which 90% of patients' least-sensitive-posture thresholds $T_{LS}$ lie when stimulated at the pulse width pw1. The shaded area 1330 therefore represents 10% of the total area under the distribution 1310. It may be seen that increasing the pulse width from pw1 to pw2 compresses the distribution of Tus and thereby decreases the 90th percentile value of $T_{LS}$ from $T_{LS}(pw1, 90)$ to $T_{LS}(pw2, 90)$. Using such population statistics, a model $T_{LS}(pw, P)$ may be constructed allowing $T_{LS}$ to be estimated for any values of pw and P within certain ranges. The model $T_{LS}(pw, P)$ will be monotonic with respect to both pw and P within certain ranges.

Equation (7) may then be applied to the estimated value of $T_{LS}$ to estimate the closed-loop current requirement $I_{CLC}$ of the patient for any values of pw and P within certain ranges.

Step 1270 may therefore choose a near-unity value of P and apply the model $T_{LS}(pw, P)$ together with Equation (7) to find a pulse width such the closed-loop current requirement $I_{CLC}$ of the patient is likely to be less than the out-of-compliance current limit $I_{OOC}$. For example, if P is set to 95%, a value of pulse width may be selected such that there is only a 1 in 20 (1-P) chance that the closed-loop current requirement $I_{CLC}$ of the patient will exceed the out-of-compliance current limit $I_{OOC}$.

Figure 14:
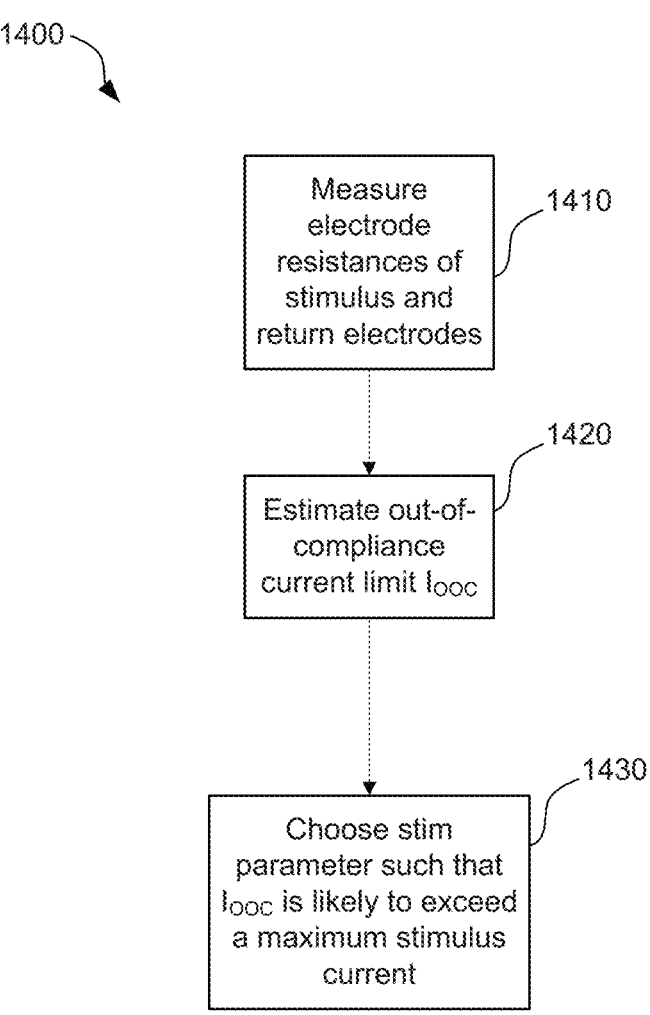
FIG. 14 is a flow chart illustrating a method of preemptively mitigating the risk of out-of-compliance events for a neural stimulation device according to one implementation of the present technology.

In an alternative implementation, the ECAP threshold need not be measured at all. Instead, the population statistics may be used to prospectively set the stimulus parameters, in particular the pulse width, to mitigate the risk of OOC events during neural stimulation programming or therapy. FIG. 14 is a flow chart illustrating a method 1400 of pre-emptively mitigating the risk of out-of-compliance events in a neural stimulation device according to such an implementation of the present technology. The method 1400 may be carried out during programming of a neuromodulation device by the APM, the APF, or a combination of both as described above.

The method 1400 starts at step 1410, which measures the electrode resistances of the stimulus electrode(s) and return electrode(s) of the current SEC specified by the current therapy parameters. Step 1420 then applies equation (6), and possibly equation (4) if there is more than one return electrode in the SEC, to estimate the out-of-compliance current limit $I_{OOC}$ for each stimulus electrode in the SEC.

The method 1400 then proceeds to step 1430, which uses population statistics to choose one or more stimulus parameters such that the out-of-compliance current limit $I_{OOC}$ is likely to exceed a maximum stimulus current expected to be used during neural stimulation device programming or therapy. In one implementation, suitable for closed-loop neural stimulation devices, the maximum stimulus current is the closed-loop current requirement $I_{CLC}$ for closed-loop neural stimulation therapy. In such an implementation, step 1430 uses a model of $I_{CLC}$ as a function of percentile and pulse width to select a pulse width such that the out-of-compliance current limit $I_{OOC}$ is likely to exceed the closed-loop current requirement $I_{CLC}$. For example, if $I_{OOC}$ is equal to 20 mA, step 1430 may set P to 95% and thereby select a pulse width such that there is only a 1 in 20 chance that the closed-loop current requirement $I_{CLC}$ of the patient will exceed 20 mA.

In other implementations, step 1430 uses population statistics to choose one or more stimulus parameters such that the out-of-compliance current limit $I_{OOC}$ is likely to exceed a maximum stimulus current expected to be used during programming a neural stimulation device, whether the device is closed-loop or open-loop. In one example, programming a neural stimulation device comprises ramping stimulus intensity to a patient's discomfort threshold, which is not known in advance. In such an example, the maximum stimulus current is the discomfort threshold, and step 1430 may use population statistics about discomfort thresholds at different pulse widths to infer a pulse width at which $I_{OOC}$ is likely to exceed the discomfort threshold. In other examples of step 1430, population statistics of discomfort thresholds in relation to parameters other than pulse width that influence discomfort threshold may be used to set a value for such parameters at which $I_{OOC}$ is likely to exceed the discomfort threshold.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

| LABEL LIST | |
| --- | --- |
| stimulator | 100 |
| patient | 108 |
| electronics module | 110 |
| battery | 112 |
| telemetry module | 114 |
| controller | 116 |
| memory | 118 |
| clinical data | 120 |
| clinical settings | 121 |
| control programs | 122 |
| pulse generator | 124 |
| electrode selection module | 126 |
| measurement circuitry | 128 |
| system ground | 130 |
| electrode array | 150 |
| biphasic stimulus pulse | 160 |
| neural response | 170 |
| nerve | 180 |
| communications channel | 190 |
| external computing device | 192 |
| system | 300 |
| clinical settings controller | 302 |
| target ECAP controller | 304 |
| box | 308 |
| box | 309 |
| controller | 310 |
| box | 311 |
| stimulator | 312 |
| element | 313 |
| measurement circuitry | 318 |
| signal window | 319 |
| ECAP detector | 320 |
| comparator | 324 |
| gain element | 336 |
| integrator | 338 |
| activation plot | 402 |
| ECAP threshold | 404 |
| discomfort threshold | 408 |
| perception threshold | 410 |
| therapeutic range | 412 |
| activation plot | 502 |
| activation plot | 504 |
| activation plot | 506 |
| ECAP threshold | 508 |
| ECAP threshold | 510 |
| ECAP threshold | 512 |
| ECAP target | 520 |
| ECAP | 600 |
| neural stimulation system | 700 |
| device | 710 |
| remote controller | 720 |
| CST | 730 |
| CI | 740 |
| charger | 750 |

-continued

LABEL LIST

| | |
|---|---|
| model | 800 |
| CPE | 810 |
| current source | 820 |
| resistor mesh | 830 |
| load resistance | 910 |
| star network | 920 |
| star point | 930 |
| circuit representation | 1000 |
| current source | 1020 - 1 |
| current source | 1020 - 2 |
| current source | 1020 - x |
| point | 1010 |
| graph | 1100 |
| curve | 1110 |
| method | 1200 |
| step | 1210 |
| step | 1220 |
| step | 1230 |
| step | 1240 |
| step | 1250 |
| step | 1260 |
| step | 1270 |
| graph | 1300 |
| distribution | 1310 |
| distribution | 1320 |
| area | 1330 |
| method | 1400 |
| step | 1410 |
| step | 1420 |
| step | 1430 |

The invention claimed is:

1. A neural stimulation system comprising:

an implantable device for controllably delivering neural stimuli, the device comprising:

a plurality of electrodes including one or more stimulus electrodes and one or more measurement electrodes;

a stimulus source configured to provide neural stimuli to be delivered via the one or more stimulus electrodes to a neural pathway of a patient in order to evoke neural responses from the neural pathway;

measurement circuitry configured to capture signal windows from signals sensed on the neural pathway via the one or more measurement electrodes subsequent to respective neural stimuli; and a control unit configured to:

control the stimulus source to provide a neural stimulus according to a stimulus intensity parameter;

measure an intensity of an evoked neural response in a captured signal window subsequent to the neural stimulus;

compute a feedback variable from the measured intensity of the evoked neural response; and adjust, using a feedback controller, the stimulus intensity parameter so as to maintain the feedback variable at a target response intensity; and a processor configured to:

estimate an out-of-compliance current limit for each of the one or more stimulus electrodes;

estimate a closed-loop current requirement for the implantable device;

compare the out-of-compliance current limit for each of the one or more stimulus electrodes to the closed-loop current requirement; and take a mitigating action based on the comparison.

2. The system of claim 1, wherein the processor is configured to estimate the out-of-compliance current limit for a stimulus electrode by:

measuring an electrode resistance of the stimulus electrode; and estimating the out-of-compliance current limit for the stimulus electrode using the measured electrode resistance of the stimulus electrode.

3. The system of claim 1, wherein the processor is configured to estimate the closed-loop current requirement for the implantable device by:

estimating a threshold value of the stimulus intensity parameter; and estimating the closed-loop current requirement by applying a model to the estimated threshold value.

4. The system of claim 1, wherein the processor is configured to estimate the closed-loop current requirement for the implantable device from a pulse width of the provided neural stimuli.

5. The system of claim 1, wherein the processor is configured to take the mitigation action upon the closed-loop current requirement for the implantable device exceeding the out-of-compliance current limit for at least one stimulus electrode of the one or more stimulus electrodes.

6. The system of claim 5, wherein the mitigation action comprises increasing the out-of-compliance current limit for the at least one stimulus electrode of the one or more stimulus electrodes.

7. The system of claim 6, wherein the processor is configured to increase the out-of-compliance current limit by increasing a number of return electrodes via which the neural stimulus current is returned from the neural pathway.

8. The system of claim 6, wherein the processor is configured to increase the out-of-compliance current limit by selecting an alternative stimulus electrode to the at least one stimulus electrode of the one or more stimulus electrodes.

9. The system of claim 5, wherein the mitigation action comprises decreasing the closed-loop current requirement for the implantable device.

10. The system of claim 9, wherein the processor is configured to decrease the closed-loop current requirement by increasing a pulse width of the provided neural stimuli.

11. The system of claim 10, wherein the processor is configured to use population statistics to increase the pulse width such that the out-of-compliance current limit for a stimulus electrode is likely to exceed the closed-loop current requirement for the implantable device.

12. An automated method of controllably delivering neural stimuli to a neural pathway of a patient, the method comprising:

delivering a neural stimulus to the neural pathway of the patient in order to evoke a neural response from the neural pathway, the neural stimulus being delivered according to a stimulus intensity parameter via one or more stimulus electrodes;

capturing a signal window from a signal sensed on the neural pathway subsequent to the delivered neural stimulus;

measuring an intensity of a neural response evoked by the delivered neural stimulus in the captured signal window;

computing, from the measured intensity of the evoked neural response, a feedback variable;

adjusting the stimulus intensity parameter so as to maintain the feedback variable at a target response intensity;

estimating an out-of-compliance current limit for each of the one or more stimulus electrodes;

estimating a closed-loop current requirement;

comparing the out-of-compliance current limit for each of the one or more stimulus electrodes to the closed-loop current requirement; and taking a mitigating action based on the comparison.

13. The method of claim 12, wherein estimating the out-of-compliance current limit for a stimulus electrode by:

measuring an electrode resistance of the stimulus electrode; and estimating the out-of-compliance current limit for the stimulus electrode using the measured electrode resistance of the stimulus electrode.

14. The method of claim 12, wherein estimating the closed-loop current comprises:

estimating a threshold value of the stimulus intensity parameter; and estimating the closed-loop current requirement by applying a model to the estimated threshold value.

15. The method of claim 12, wherein taking a mitigating action based on the comparison comprises taking the mitigation action upon the closed-loop current requirement exceeding the out-of-compliance current limit for at least one stimulus electrode of the one or more stimulus electrodes.

16. The method of claim 15, wherein the mitigation action comprises increasing the out-of-compliance current limit for the at least one stimulus electrode of the one or more stimulus electrodes.

17. The method of claim 16, wherein increasing the out-of-compliance current limit comprises increasing a number of return electrodes via which the neural stimulus current is returned from the neural pathway.

18. The method of claim 15, wherein the mitigation action comprises decreasing the closed-loop current requirement.

19. The method of claim 18, wherein decreasing the closed-loop current requirement comprises increasing a pulse width of the neural stimuli.

20. A neural stimulation system comprising:

an implantable closed-loop neural stimulation device for controllably delivering neural stimuli via one or more stimulus electrodes, the device comprising the one or more stimulus electrodes and a feedback controller configured to adjust a stimulus intensity parameter so as to maintain a measured neural response intensity at a target response intensity; and a processor configured to:

estimate an out-of-compliance current limit for each of the one or more stimulus electrodes;

estimate a closed-loop current requirement for the implantable closed-loop neural stimulation device;

compare the out-of-compliance current limit for each of the one or more stimulus electrodes to the closed-loop current requirement; and take a mitigating action based on the comparison.

* * * * *